(12) United States Patent
Hai et al.

(10) Patent No.: US 10,428,200 B2
(45) Date of Patent: *Oct. 1, 2019

(54) IMMOBILIZATION OF AN ACTIVE AGENT ON A SUBSTRATE USING COMPOUNDS INCLUDING TRIHYDROXYPHENYL GROUPS

(71) Applicants: BAXTER INTERNATIONAL INC., Deerfield, IL (US); BAXTER HEALTHCARE SA, Glattpark (Opfikon) (CH); NORTHWESTERN UNIVERSITY, Evanston, IL (US)

(72) Inventors: Ton That Hai, Round Lake, IL (US); John-Bruce Devault Green, Buffalo Grove, IL (US); Timothy Michael Fulghum, Lakemoor, IL (US); Phillip Byron Messersmith, Clarendon Hills, IL (US); Tadas Stanislovas Sileika, Northbrook, IL (US)

(73) Assignees: Baxter International Inc., Deerfield, IL (US); Baxter Healthcare SA, Glattpark (Opfikon) (CH); Northwestern University, Evanston, IL (US)

( * ) Notice: Subject to any disclaimer, the term of this patent is extended or adjusted under 35 U.S.C. 154(b) by 10 days.

This patent is subject to a terminal disclaimer.

(21) Appl. No.: 15/490,412

(22) Filed: Apr. 18, 2017

(65) Prior Publication Data

US 2017/0218174 A1 Aug. 3, 2017

Related U.S. Application Data

(62) Division of application No. 14/298,693, filed on Jun. 6, 2014, now Pat. No. 9,655,917.

(Continued)

(51) Int. Cl.

| | |
|---|---|
| *C08K 5/13* | (2006.01) |
| *A61L 31/16* | (2006.01) |
| *A61L 31/04* | (2006.01) |
| *A61L 31/06* | (2006.01) |
| *A61K 31/05* | (2006.01) |
| *A61K 31/08* | (2006.01) |
| *A61K 31/11* | (2006.01) |
| *A61K 31/132* | (2006.01) |
| *A61K 31/194* | (2006.01) |
| *A61K 31/722* | (2006.01) |
| *A61K 47/02* | (2006.01) |
| *G01N 33/543* | (2006.01) |
| *G01N 33/551* | (2006.01) |
| *A61L 27/34* | (2006.01) |
| *A61L 27/54* | (2006.01) |

(Continued)

(52) U.S. Cl.
CPC ............ *C08K 5/13* (2013.01); *A61K 31/05* (2013.01); *A61K 31/08* (2013.01); *A61K 31/11* (2013.01); *A61K 31/132* (2013.01); *A61K 31/194* (2013.01); *A61K 31/722* (2013.01); *A61K 47/02* (2013.01); *A61K 47/58* (2017.08); *A61K 47/59* (2017.08); *A61L 27/34* (2013.01); *A61L 27/54* (2013.01); *A61L 29/085* (2013.01); *A61L 29/16* (2013.01); *A61L 31/042* (2013.01); *A61L 31/06* (2013.01); *A61L 31/10* (2013.01); *A61L 31/16* (2013.01); *G01N 33/54353* (2013.01); *G01N 33/551* (2013.01); *A61L 2300/404* (2013.01)

(58) Field of Classification Search
None
See application file for complete search history.

(56) References Cited

U.S. PATENT DOCUMENTS

| | | |
|---|---|---|
| 3,425,418 A | 2/1969 | Chvapil |
| 4,051,302 A | 9/1977 | Mayama et al. |

(Continued)

FOREIGN PATENT DOCUMENTS

| | | |
|---|---|---|
| CN | 101801429 A | 8/2010 |
| CN | 102834123 A | 12/2012 |

(Continued)

OTHER PUBLICATIONS

Dorniani et al. Preparation of Fe3O4 magnetic nanoparticles coated with gallic acid for drug delivery.*

(Continued)

*Primary Examiner* — Robert A Wax
*Assistant Examiner* — Danah Al-Awadi
(74) *Attorney, Agent, or Firm* — K&L Gates LLP

(57) ABSTRACT

The invention provides methods of immobilizing an active agent to a substrate surface, including the steps of, providing a substrate, contacting the substrate with a solution of a compound including a trihydroxyphenyl group, thereby forming a trihydroxyphenyl-treated substrate, and contacting the trihydroxyphenyl-treated substrate with an active agent, thereby immobilizing the active agent on the substrate. Further provided are methods of immobilizing an active agent on a substrate, including the steps of providing a substrate, combining a solution of a compound including a trihydroxyphenyl group with a solution of an active agent, thereby forming a solution of an active agent-trihydroxyphenyl conjugate, and contacting the substrate with the solution of the active agent-trihydroxyphenyl conjugate, thereby immobilizing the active agent on the substrate. The invention further provides substrates and medical device or device components with active agents immobilized on the surface thereof.

17 Claims, No Drawings

Related U.S. Application Data

(60) Provisional application No. 61/832,477, filed on Jun. 7, 2013, provisional application No. 61/832,488, filed on Jun. 7, 2013.

(51) Int. Cl.

| | |
|---|---|
| A61L 29/08 | (2006.01) |
| A61L 29/16 | (2006.01) |
| A61L 31/10 | (2006.01) |
| A61K 47/58 | (2017.01) |
| A61K 47/59 | (2017.01) |

(56) References Cited

U.S. PATENT DOCUMENTS

| | | | |
|---|---|---|---|
| 5,242,432 A | 9/1993 | DeFrank | |
| 5,360,413 A | 11/1994 | Leason et al. | |
| 5,730,418 A | 3/1998 | Feith et al. | |
| 5,782,816 A | 7/1998 | Werschmidt et al. | |
| 6,039,302 A | 3/2000 | Cote, Sr. et al. | |
| 6,669,681 B2 | 12/2003 | Jepson et al. | |
| 6,682,509 B2 | 1/2004 | Lopez | |
| 7,618,937 B2 | 11/2009 | Messersmith et al. | |
| 7,622,533 B2 | 11/2009 | Lee | |
| 7,682,669 B1* | 3/2010 | Michal | A61L 31/10 427/2.24 |
| 8,119,742 B2 | 2/2012 | Dalsin et al. | |
| 9,125,973 B2 | 9/2015 | Bui et al. | |
| 2003/0141477 A1 | 7/2003 | Miller | |
| 2003/0208165 A1 | 11/2003 | Christensen et al. | |
| 2006/0009550 A1 | 1/2006 | Messersmith et al. | |
| 2007/0282422 A1 | 12/2007 | Biggs et al. | |
| 2008/0021381 A1 | 1/2008 | Lurvey et al. | |
| 2008/0021392 A1 | 1/2008 | Lurvey et al. | |
| 2008/0169059 A1 | 7/2008 | Messersmith et al. | |
| 2008/0247984 A1 | 10/2008 | Messersmith et al. | |
| 2009/0024096 A1 | 1/2009 | Hai et al. | |
| 2009/0105629 A1 | 4/2009 | Grant et al. | |
| 2009/0123652 A1 | 5/2009 | Messersmith et al. | |
| 2010/0028719 A1 | 2/2010 | Messersmith et al. | |
| 2010/0063153 A1 | 3/2010 | Chatterjee et al. | |
| 2010/0113828 A1 | 5/2010 | Dalsin et al. | |
| 2010/0137902 A1 | 6/2010 | Lee et al. | |
| 2010/0137903 A1 | 6/2010 | Lee et al. | |
| 2010/0197868 A1 | 8/2010 | Lee | |
| 2010/0297745 A1 | 11/2010 | Li et al. | |
| 2011/0009955 A1 | 1/2011 | Horres et al. | |
| 2011/0046255 A1 | 2/2011 | Rooijmans | |
| 2011/0065085 A1* | 3/2011 | Biran | A61L 27/54 435/4 |
| 2011/0318380 A1 | 12/2011 | Brix et al. | |
| 2012/0116424 A1 | 5/2012 | Lee et al. | |
| 2012/0149849 A1 | 6/2012 | Dalsin et al. | |
| 2013/0052236 A1* | 2/2013 | Tessmar | A61L 31/10 424/400 |
| 2013/0224795 A1 | 8/2013 | Park et al. | |
| 2014/0206630 A1* | 7/2014 | Messersmith | C08J 7/065 514/25 |
| 2014/0287016 A1* | 9/2014 | Hai | A61L 33/08 424/423 |
| 2014/0364391 A1 | 12/2014 | Hai et al. | |

FOREIGN PATENT DOCUMENTS

| | | | |
|---|---|---|---|
| EP | 1043720 A1 | 10/2000 | |
| EP | 1829566 A1 | 9/2007 | |
| JP | 2004/217540 A | 8/2004 | |
| JP | 2007-527871 A | 10/2007 | |
| JP | 2008253707 A | 10/2008 | |
| JP | 2010-189649 A | 9/2010 | |
| SU | 1779263 | 11/1992 | |
| WO | WO 2004014453 | * 8/2003 | |
| WO | 2010/037395 A2 | 4/2010 | |
| WO | WO-2012064821 A2 | 5/2012 | |
| WO | WO-2012113058 | 8/2012 | |
| WO | WO-2012/158944 A1 | 11/2012 | |
| WO | WO-2013/053809 A1 | 4/2013 | |
| WO | WO 20131729666 | * 11/2013 | |

OTHER PUBLICATIONS

Agarwal et al., Gallic acid causes inactivating phosphorylation of cdc25A/cdc25C-cdc2 via ATM-Chk2 activation, leading to cell cycle arrest, and induces apoptosis in human prostate carcinoma DU145 cells, Mol. Cancer Ther., 5(12):3294-302 (2006).

Chen et al., A simple one-step modification of various materials for introducing effective multifunctional groups, Colloids Surf. B Biointerfaces, 113:125-33 (2014).

Davis et al., Immobilization of RGD to < 1 1 1 > silicon surfaces for enhanced cell adhesion and proliferation, Biomaterials 23(19):4019-27 (2002).

Dorniani et al., Preparation of $Fe_3O_4$ magnetic nanoparticles coated with gallic acid for drug delivery, Int. J. Nanomedicine, 7:5745-56 (2012).

Ebara et al., Surface modification of microfluidic channels by UV-mediated graft polymerization of non-fouling and "smart" polymers, Radiation Physics and Chem., 76(8-9):1409-13 (2007).

Ebara et al., Switchable surface traps for injectable bead-based chromatography in PDMS microfluidic channels, Lab Chip, 6(7):843-8 (2006).

Faried et al., Anticancer effects of gallic acid isolated from Indonesian herbal medicine, Phaleria macrocarpa (Scheff.) Boerl, on human cancer cell lines, Int. J. Oncol., 30(3):605-13 (2007).

First Office Action (with English translation), Chinese patent application No. 201480015897.3, dated Sep. 21, 2016.

Goda et al., Biomimetic phosphorylcholine polymer grafting from polydimethylsiloxane surface using photo-induced polymerization, Biomaterials, 27(3):5151-60 (2006).

Goda et al., Photografting of 2-methacryloyloxyethyl phosphorylcholine from polydimethylsiloxane: Tunable protein repellency and lubrication property, Colloids and Surfaces B: Biointerfaces, 63(1):64-72 (2008).

Hu et al., Surface modification of poly(dimethylsiloxane) microfluidic devices by ultraviolet polymer grafting, Anal. Chem., 74(16):4117-23 (2002).

Hu et al., Surface-directed, graft polymerization within microfluidic channels, Anal. Chem., 76(7):1865-70 (2004).

Inoue et al., Role of reactive oxygen species in gallic acid-induced apoptosis, Biol. Pharm. Bull., 23(10):1153-7 (2000).

International Search Report and Written Opinion, International Application No. PCT/US2014/041240, dated Oct. 10, 2014.

Kang et al., Inhibitory effect of methyl gallate and gallic acid on oral bacteria, J. Microbiol., 46(6):744-50 (2008).

Kaur et al., Gallic acid, an active constituent of grape seed extract, exhibits anti-proliferative, proapoptotic and anti-tumorigenic effects against prostate carcinoma xenograft growth in nude mice, Pharm. Res., 26(9):2133-40 (2009).

Kawada et al., Anti-tumor effect of gallic acid on LL-2 lung cancer cells transplanted in mice, Anticancer Drugs, 12(10):847-52 (2001).

Kim et al., Gallic acid inhibits histamine release and pro-inflammatory cytokine production in mast cells, Toxicol. Sci., 91(1):123-31 (2006).

Kratz et al., Evaluation of anti-HSV-2 activity of gallic acid and pentyl gallate, Biol. Pharm. Bull., 31(5):903-7 (2008).

Luo et al., Improved immobilization of biomolecules to quinone-rich polydopamine for efficient surface functionalization, Colloids Surf. B. Biointerfaces, 106:66-73 (2013).

Luo et al., In vitro investigation of enhanced hemocompatibility and endothelial cell proliferation associated with quinone-rich polydopamine coating, ACS Appl. Mater. Interfaces, 5(5):1704-14 (2013).

Ma et al., Preparation and characterization of thermo-responsive PDMS surfaces grafted with poly(N-isopropylacrylamide) by benzophenone-initiated photopolymerization, J. Colloid Interface Sci., 332(1):85-90 (2009).

Mourya et al., Chitosan modifications and applications: Opportunities galore, Reactive Functional Polymers, 68(6):1013-51 (2008).

(56) References Cited

OTHER PUBLICATIONS

Ohno et al., Induction of apoptosis by gallic acid in lung cancer cells, Anticancer Drugs, 10(9):845-51 (1999).
Rajalakshmi et al., Assessment of the no-observed-adverse-effect level (NOAEL) of gallic acid in mice, Food Chem. Toxicol., 39(9):919-22 (2001).
Serrano et al., Double-edged sword behaviour of gallic acid and its interaction with peroxidases in human microvascular endothelial cell culture (HMEC-1). Antioxidant and pro-oxidant effects, Acta Bichim. Pol., 57(2):193-8 (2010).
Strlic et al., Anti- and prooxidative properties of gallic acid in fenton-type systems, J. Agric. Food Chem., 50(22):6313-7 (2002).
Sui et al., Solution-phase surface modification in intact poly(dimethylsiloxane) microfluidic channels, Anal. Chem., 78(15):5543-51 (2006).
Vartiainen et al., Tyorsinase-catalysed grafting of food-grade gallates to chitosan: surface properties of novel functional coatings, Packaging Technology and Science, 21(6):317-28 (2008).
Veluri et al., Fractionation of grape seed extract and identification of gallic acid as one of the major active constituents causing growth inhibition and apoptotic death of DU145 human prostate carcinoma cells, Carcinogenesis, 27(7):1445-53 (2006).
Wang et al., Covalent micropatterning of poly(dimethylsiloxane) by photografting through a mask, Anal. Chem., 77(23):7539-46 (2005).
Yang et al., Construction of polyfunctional coatings assisted by gallic acid to facilitate co-immobilization of diverse biomolecules, ACS Appl. Mater. Interfaces, 5(21):10495-501 (2013).
You et al., Gallic acid-induced lung cancer cell death is related to glutathione depletion as well as reactive oxygen species increase, Toxicol. in Vitro, 24(5):1356-62 (2010).

\* cited by examiner

IMMOBILIZATION OF AN ACTIVE AGENT ON A SUBSTRATE USING COMPOUNDS INCLUDING TRIHYDROXYPHENYL GROUPS

NAMES OF PARTIES TO A JOINT RESEARCH AGREEMENT

The claimed invention was made as a result of activities undertaken within the scope of a joint research agreement between Baxter Healthcare Corporation and Northwestern University.

FIELD OF THE INVENTION

The invention relates generally to the immobilization of an active agent on a substrate. More particularly, the invention relates to methods of immobilizing an active agent on a substrate through the coupling of a compound including a trihydroxyphenyl group, having an active agent coupled thereto, with/to the substrate, substrates with active agents immobilized thereto, and medical devices comprising substrates with active agents immobilized thereto.

BRIEF DESCRIPTION OF RELATED TECHNOLOGY

Medical devices and medical device components that are used for hemodialysis or other applications that involve contact between physiologic fluids, such as blood, or tissue and the medical device or device component are known to become fouled with protein, cell, and/or bacterial deposits from the contact. The deposition of protein from the blood onto medical devices or medical device components is problematic for a number of materials commonly used as substrates for medical devices and medical device components, especially polysulfone, polycarbonate, and silicone. In many cases, the fouling can impair function or lead to failure of the medical device. This problem is particularly significant for extracorporeal blood circuits and components thereof such as the tubing used in a hemodialysis set.

Coating substrates with active agents, for example, antifouling/antimicrobial agents, is known in the art. For example, 3,4-dihydroxyphenylalanine (DOPA) has been used to synthesize dihydroxyphenyl containing polymers which can be used as adhesive polymers which also provide antifouling/antimicrobial coatings, as described in U.S. Pat. No. 7,618,937, and U.S. Patent Application Publication Nos. 2010/0028719, 2009/0123652, 2008/0247984, 2008/0169059, and 2006/0009550. Typically, the polymers derived from DOPA comprise anchor moieties comprised of peptides, such as lysine, copolymerized with DOPA, as shown in structure (I) below, which can be costly to mass produce. It is believed that a peptide or peptoid moiety, coupled to the anchor moiety is generally resistant to, or inhibits protein adsorption, or cell fouling of the surfaces onto which the composition is coated or attached.

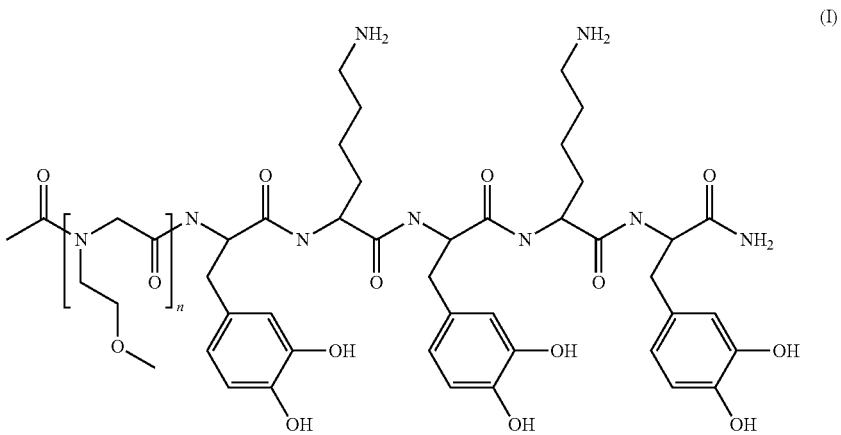

(I)

Alternatively, U.S. Pat. No. 7,622,533 and U.S. Patent Application Publication No. 2010/0197868 describe an adhesive polymer including pendant DOPA groups or dihydroxyphenyl (DHDP) derivatives attached thereto to form adhesive polymers capable of binding to a dissimilar substrate, as shown in structure (II) below.

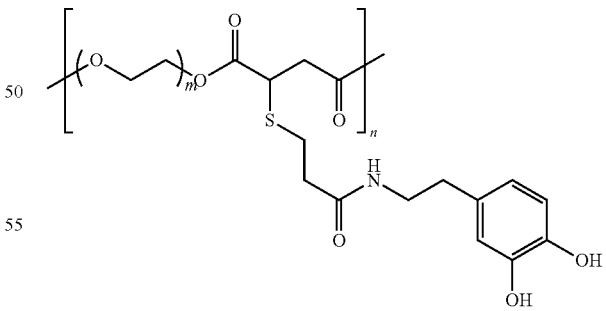

(II)

However, with both approaches, leaching of the DOPA from the polymer is a significant toxicity concern.

SUMMARY

The invention provides methods of immobilizing an active agent on a substrate surface, including the steps of providing a substrate, contacting the substrate with a solution of a compound including a trihydroxyphenyl group thereby coupling the trihydroxyphenyl group to the substrate to provide a trihydroxyphenyl-treated substrate, and contacting the trihydroxyphenyl treated-substrate with an active agent, to couple the active agent to the trihydroxyphenyl treated substrate thereby immobilizing the active agent on the substrate surface. The method can optionally include a step of activating the substrate so as to introduce a reactive moiety on a surface of the substrate, prior to contacting the substrate with the solution of the compound including a trihydroxyphenyl group. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group.

In a related aspect, the invention further provides methods of immobilizing an active agent on a substrate, including the steps of providing a substrate, combining in solution a compound including a trihydroxyphenyl group and an active agent, thereby forming a solution of an active agent-trihydroxyphenyl conjugate, and contacting the substrate with the solution of the active agent-trihydroxyphenyl conjugate thereby coupling the trihydroxyphenyl group of the active agent-trihydroxyphenyl conjugate to the substrate, and immobilizing the active agent on the substrate surface. The method can optionally include a step of activating the substrate so as to introduce a reactive moiety on a surface of the substrate, prior to contacting the substrate with the active agent-trihydroxyphenyl conjugate. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group.

In another related aspect, the invention provides substrates having an active agent immobilized on a surface thereof, the substrate having a compound including a trihydroxyphenyl group coupled to the substrate surface, wherein the compound includes an active agent coupled thereto so as to immobilize the active agent on the substrate. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group.

In another related aspect, the invention provides medical devices including a substrate according to the invention.

Further aspects of the invention may become apparent to those skilled in the art from a review of the following detailed description, taken in conjunction with the appended claims. While the invention is susceptible of embodiments in various forms, described hereinafter are specific embodiments of the invention with the understanding that the disclosure is illustrative, and is not intended to limit the invention to specific embodiments described herein.

DETAILED DESCRIPTION

The invention provides substrates with an active agent advantageously and securely immobilized on a surface thereof and methods for forming same. The substrates with an active agent immobilized thereto are particularly advantageous in that they can be produced relatively inexpensively, particularly relative to prior art substrates coated with adhesive polymers derived from peptide-DOPA copolymers. The substrates with active agents immobilized thereto can also be particularly advantageous in that they demonstrate low toxicity, particularly relative to prior art substrates coated using DOPA-based adhesive polymers.

The invention provides methods of immobilizing an active agent on a substrate surface, including the steps of providing a substrate, contacting the substrate with a solution of a compound including a trihydroxyphenyl group to couple the trihydroxyphenyl group to the substrate, to provide a trihydroxyphenyl-treated substrate, and contacting the trihydroxyphenyl-treated substrate with an active agent to couple the active agent to the trihydroxyphenyl-treated substrate, thereby immobilizing the active agent on the substrate. The method can optionally include a step of activating the substrate so as to introduce a reactive moiety on a surface of the substrate, prior to contacting the substrate with the solution of the compound include a trihydroxyphenyl group. The methods can further include the step of contacting the trihydroxyphenyl-treated substrate with a solution of a linker compound thereby coupling the linker compound to the trihydroxyphenyl group of the trihydroxyphenyl-treated substrate, prior to contacting the trihydroxyphenyl-treated substrate with the active agent.

Optionally, the methods include the methods of immobilizing an active agent on a substrate having a metallic surface. Typically, while not intending to be bound by theory, it is believed that the trihydroxyphenyl group of the compound including the trihydroxyphenyl group is coupled to the metallic substrate by forming two or more bonds between the trihydroxyphenyl group and a metal ion of the metallic substrate surface, thereby chelating the trihydroxyphenyl group to the metallic substrate surface (and thus essentially the substrate itself). As used herein, "substrate having a metallic surface" encompasses a substrate that includes a coating of a metal, for example, a substrate that has been metallized, as well as a substrate consisting essentially of metal. The metallic surface can be a metal oxide surface. The metallic and/or metal oxide surface generally includes metal ions.

As used herein, "immobilizing" or "immobilized" encompasses any of securing, attaching, affixing, connecting, and/or joining, an active agent to a substrate surface. Immobilization of the active agent to the substrate surface can be confirmed using a number of different techniques. For example, the immobilization of the active agent can be confirmed by demonstrating that the activity of the active agent is present using assays known in the art. The activity of the active agent can be assessed with functional assays. For example, a thrombogenic assay can be used to detect anti-thrombogenic agents such as heparin, 4-hydroxycoumarin, and the like. Further, for example, the active agent may be labeled with a fluorescent dye, an isotopic label, or a radiolabel that can be detected on the substrate when the active agent is immobilized thereto. The presence of the active agent can also be determined with surface spectroscopies such as x-ray photoelectron spectroscopy (XPS), Fourier transform infrared reflection-absorption spectroscopy (FTIRRAS), and Raman spectroscopy. Further, cationic stains can be used to confirm/detect the presence of anionic active agents, for example, Alcian blue and Toluidine blue form a complex with anionic active agents such as heparin.

As used herein, "chelation" and "chelating" encompasses the formation or presence of two or more separate bonds between a polydentate ligand, such as a trihydroxyphenyl group, and a single metal ion via the hydroxyls of the trihydroxyphenyl group. The two or more separate bonds are generally considered to be ionic bonds and can include coordinate bonds, dative bonds, dipolar bonds, and the like. The chelation of the hydroxyls of the trihydroxyphenyl group to a metal ion of the metallic substrate surface can be confirmed by providing a thin film, such as a monolayer of the compound including the trihydroxyphenyl group, on the substrate having a metallic surface and using Fourier transform infrared spectroscopy (FTIR), Fourier transform infrared reflection-absorption spectroscopy (FTIRRAS), Raman spectroscopy, or cyclic voltammetry to confirm chelation. When the compound including the trihydroxyphenyl group is coupled to the metallic surface at a thickness greater than one monolayer, it is expected that the first monolayer of the compound including the trihydroxyphenyl group will chelate to the surface in the same way as a thin film prepared with only a monolayer.

As used herein, "coupling" and "couple" encompass any of covalent bond formation, hydrogen bond formation, ionic bond formation (e.g., electrostatic attraction), and van der Waals interactions, for example, through which the compound including a trihydroxyphenyl group can adsorb to/adhere to/couple to/associate with a substrate surface or a linker compound, and through which the active agent can adsorb to/adhere to/couple to/associate with a compound including a trihydroxyphenyl group or a linker compound.

As used herein, "compound including a trihydroxyphenyl group" encompasses small molecule compounds, polymers including trihydroxyphenyl groups, and trihydroxyphenyl-linker conjugates. The polymers including trihydroxyphenyl groups include polymers wherein the trihydroxyphenyl group is in the polymer backbone and polymers including at least one monomer having a pendant trihydroxyphenyl group.

As used herein, "trihydroxyphenyl group" refers to a compound comprising a phenyl ring substituted with at least three hydroxyls. The trihydroxyphenyl group therefore includes compounds comprising a phenyl ring substituted with three hydroxyls, and even with four hydroxyls. Generally, compounds comprising a phenyl ring substituted with three hydroxyls are preferred. Compounds comprising a phenyl ring substituted with three hydroxyls are advantageous because in addition to the three hydroxyl groups, such compounds have three potential sites of reactivity available, which sites can be selected from but are not limited to unsubstituted carbons of the phenyl moiety of the trihydroxyphenyl group and other reactive covalently bonded to the phenyl moiety of the trihydroxyphenyl group. For example, two unsubstituted carbons and/or reactive groups can couple the compound including a trihydroxyphenyl group to a substrate surface and an active agent, a substrate and a linker compound, or to two additional compounds including a trihydroxyphenyl group via sites of reactivity on the additional trihydroxyphenyl groups (i.e., resulting in polymer formation). A compound with a third site of reactivity, in addition to the coupling that can be done with two sites of reactivity, can advantageously also couple to a linker compound, an active agent, or another compound including a trihydroxyphenyl, and can be particularly advantageous for crosslinking of polymers including trihydroxyphenyl groups. Further, without intending to be bound by any particular theory, it is believed that compounds comprising a phenyl ring substituted with three hydroxyls are advantageous over compounds having one or two hydroxyls because typically the unsubstituted carbons on the phenyl moiety of the compounds comprising three hydroxyls are relatively more reactive. For example, as the number of hydroxyls on the phenyl ring increases, the rate of oxidation generally increases and thus it is relatively easier for compounds containing trihydroxyphenyl groups to form quinone-like species than corresponding compounds having phenyl groups substituted with only one or two hydroxyls. Consequently, compounds comprising a phenyl ring substituted with at least three hydroxyls typically have unsubstituted carbons that are relatively more reactive than the unsubstituted carbons on corresponding compounds having phenyl groups substituted with only one or two hydroxyls.

As used herein, "sites of reactivity" or "reactive sites" on the compound including a trihydroxyphenyl group do not refer to the hydroxyl moieties themselves, but refer to any other site on the compound including a trihydroxyphenyl group through which an active agent, linker compound, or additional compound including a trihydroxyphenyl group can couple to the compound including a trihydroxyphenyl group. For example, sites of reactivity can include unsubstituted carbons of the phenyl moiety of the trihydroxyphenyl group and reactive groups covalently bonded to the phenyl moiety of the trihydroxyphenyl group which can include, but are not limited to, carboxyls, carboxylates, amides, acyl halides, aldehydes, ketones, and esters.

As used herein, "polymer" encompasses any compound with two or more repeat units, for example, dimers, trimers, and higher oligomers. The repeat units can be the same such that a homopolymer is provided, or different such that a copolymer is provided.

As used herein, "active agent" encompasses active agents (including those specifically mentioned herein) and active agent-linker conjugates.

As used herein, "linker compound" encompasses any compound that has at least two end groups such that the linker compound can couple to and thereby connect two separate molecules. For example, the linker compound can couple to either a reactive group and/or an unsubstituted carbon of the trihydroxyphenyl group through a first end group and to a polymerizable moiety through a second end group, so as to form a polymerizable monomer. Alternatively, the linker compound can couple to couple to either a reactive group and/or an unsubstituted carbon of the trihydroxyphenyl group through a first end group and to an active agent through a second end group so as to form a trihydroxyphenyl-linker-active agent conjugate.

As used herein, "conjugate" refers to the species that results from the coupling together of two or more of a compound including a trihydroxyphenyl group, a linker compound, and/or an active agent. The species that have been conjugated are provided immediately before the term "conjugate." The conjugate can be formed by coupling the two species that are to form a conjugate, as defined above.

In a related aspect, the invention further provides methods of immobilizing an active agent on a substrate, including the steps of providing a substrate, combining in solution a compound including a trihydroxyphenyl group and an active agent to couple the compound including a trihydroxyphenyl group and the active agent, thereby forming a solution of an active agent-trihydroxyphenyl conjugate, and contacting the substrate with the solution of the active agent-trihydroxyphenyl conjugate to couple the trihydroxyphenyl group of the active agent-trihydroxyphenyl conjugate to the substrate and thereby immobilize the active agent on the substrate. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group.

The active agent-trihydroxyphenyl conjugate can be provided as an active agent that is coupled to a linker compound that is further coupled to the trihydroxyphenyl group of the compound including the trihydroxyphenyl group.

The combining and contacting steps can be conducted simultaneously such that compound including the trihydroxyphenyl group and the active agent are combined in the presence of the substrate, or alternatively the combining and contacting steps can be conducted separately and in sequence. Optionally, the substrate treated with the methods according to the invention is a substrate having a metallic surface. Typically, while not intending to be bound by theory, it is believed that the trihydroxyphenyl group is coupled to a metallic substrate by forming two or more bonds between the trihydroxyphenyl group and a metal ion of the metallic substrate surface, thereby chelating the trihydroxyphenyl group to the metallic substrate surface (and thus essentially the substrate itself).

In another related aspect, the invention provides substrates having an active agent immobilized on a surface thereof, the substrate having a compound including a trihydroxyphenyl group coupled to the substrate surface, wherein the trihydroxyphenyl group includes an active agent coupled thereto so as to immobilize the active agent on the substrate. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group. The active agent can be coupled to the trihydroxyphenyl group via a linker compound, so as to immobilize the active agent on the substrate. Optionally, the substrate is a substrate having a metallic surface. Typically, while not intending to be bound by theory, it is believed that the trihydroxyphenyl group is chelated to the metallic substrate surface such that there are two or more bonds between the trihydroxyphenyl group and a metal ion of the metallic surface of the substrate.

In another related aspect, the invention provides medical devices including a substrate according to the invention. Medical devices and medical device components comprising substrates according to the invention can include active agents that advantageously render the device or device component antibacterial, antifouling, and/or antithrombogenic. Of course, the active agents can demonstrate other therapeutic or beneficial activities.

The medical devices and medical device components comprising active agents immobilized thereto can be particularly advantageous because the medical device or device component can be effectively "coated" by immobilizing an active agent on/to a (substrate) surface thereof, and thereby reduce the need to treat a patient with the (same or similar) active agent. For example, patients whose treatment requires an extracorporeal blood circuit, such as for hemodialysis, apheresis, or coronary bypass, are often administered heparin (or similar acting active agents) prior to the procedure so as to prevent blood clot formation in the blood circuit pumps and tubings. However, in addition to inhibiting clot formation, administration of significant amounts of heparin can render the patient susceptible to bleeding after the treatment. Therefore, it would be advantageous to use blood circuit devices with heparin immobilized thereto, thereby reducing the amount of heparin needed for treatment prior to the procedure and the attendant risk of the patient experiencing bleeding problems and/or needing extended hospitalization or medical care subsequent to the procedure.

In general, the methods according to the invention result in an active agent immobilized on a substrate surface through the use of a compound including a trihydroxyphenyl group that can couple to the substrate surface. The methods described herein can include the use of solutions of compounds including trihydroxyphenyl groups (e.g., solutions of trihydroxyphenyl-linker conjugates, solutions of small molecule compounds including trihydroxyphenyl groups such as gallic acid, and solutions of polymers including trihydroxyphenyl groups such as polygallic acid), solutions of linker compounds, solutions of active agents (including solutions of discrete active agents as well as active agent-linker conjugates), and solutions of active agent-trihydroxyphenyl conjugates. The solvents used to prepare the solutions of compounds including trihydroxyphenyl groups, solutions of linker compounds, solutions of active agents, and solutions of active agent-trihydroxyphenyl conjugates can be any solvent suitable to act as a carrier for the compounds including a trihydroxyphenyl group, linker compounds, active agents, and/or active agent-trihydroxyphenyl conjugates. For example, the solutions described herein can comprise aqueous solutions, other solvents including but not limited to, alcohols, diols, organosulfurs such as sulfolane, ethers, such as diethyl ether and tetrahydrofuran, alkanes, aromatics, halocarbons, such as chloroform and dichloromethane, and combinations of the foregoing. When the term "solution" is used herein, it is not necessary that the components contained therein completely dissolve. Thus, as used herein, the term solution encompasses both dispersions in which components are dispersed and solutions in which components are substantially or even completely dissolved. In general, complete dissolution of the component is preferred. Further, as used herein, the term "solution" includes aerosolized solutions.

In one aspect of the invention, the method of immobilizing the active agent on the substrate includes the steps of:
(a) providing a substrate with a surface;
(b) contacting the substrate with a compound including a trihydroxyphenyl group thereby coupling the trihydroxyphenyl group to the substrate surface to provide a trihydroxyphenyl-treated substrate; and
(c) contacting the trihydroxyphenyl-treated substrate with an active agent to couple the active agent to the trihydroxyphenyl group, thereby immobilizing the active agent on the substrate.

In another aspect of the invention, the method of immobilizing the active agent on the substrate includes the steps of:
(a) providing a substrate with a surface;
(b) combining in solution a compound including a trihydroxyphenyl group and an active agent to couple the trihydroxyphenyl group and the active agent, thereby forming a solution of an active agent-trihydroxyphenyl conjugate; and
(c) contacting the substrate with the solution of the active agent-trihydroxyphenyl conjugate, thereby coupling the trihydroxyphenyl group of the active agent-trihydroxyphenyl conjugate to the substrate surface and immobilizing the active agent on the substrate.

In refinements of the aforementioned embodiments, the methods further include washing the trihydroxyphenyl-treated substrate with water, thereby forming a washed trihydroxyphenyl-treated substrate, and optionally flowing an inert gas such as nitrogen over the washed trihydroxyphenyl-treated substrate, prior to contacting the trihydroxyphenyl-treated substrate with the solution of an active agent.

In another refinement of the aforementioned embodiments, the methods further include washing the substrate with the active agent immobilized on a surface thereof with water, thereby forming a washed substrate with the active agent immobilized on a surface thereof and optionally flowing an inert gas such as nitrogen over the washed substrate with the active agent immobilized on the surface thereof.

In yet another refinement of the foregoing embodiments, the methods further include the step of contacting the trihydroxyphenyl-treated substrate with a solution of a linker compound thereby coupling the linker compound to the trihydroxyphenyl group of the trihydroxyphenyl-treated substrate, prior to contacting the trihydroxyphenyl-treated substrate with the solution of active agent.

The method can be selected such that the density of the active agent-trihydroxyphenyl conjugates coupled to the substrate surface can be controlled. Without intending to be limited by any particular theory, it is believed that when the trihydroxyphenyl group is coupled to the substrate surface prior to coupling the active agent to the trihydroxyphenyl group, the resulting trihydroxyphenyl-treated substrate has a relatively dense covering of trihydroxyphenyl groups coupled to the surface. It is further believed that when an active agent-trihydroxyphenyl conjugate is formed prior to coupling the trihydroxyphenyl group to the substrate surface, the resulting substrate with an active agent immobilized thereto has a relatively lower density of active agent-trihydroxyphenyl conjugates coupled to the surface, when compared to the trihydroxyphenyl-treated substrate prepared prior to coupling the active agent to the trihydroxyphenyl group. When the active agent-trihydroxyphenyl conjugate is formed prior to coupling the trihydroxyphenyl group to the substrate, the conditions can be easily controlled by one of ordinary skill in the art such that the coupling of unsubstituted carbons of the trihydroxyphenyl group to the substrate surface is favored over the coupling of any potential binding sites present on the active agent or reactive groups on the trihydroxyphenyl group to the substrate surface.

Substrates

In general, the substrate to which the active agent is (or will be) immobilized can be any substrate. Suitable substrates can include, but are not limited to, inorganic oxides (e.g., silicas, materials conventionally known as glass), ceramics, metals including metal oxides, semiconductors, and/or polymeric substrates. Metal substrates include substrates that include a coating of a metal, for example, a substrate that has been metallized, as well as substrates consisting essentially of metal. As used herein, a "metallized substrate" refers to a substrate that has been fully or partially coated with a metal (including but not limited to non-metal substrates which have been modified to include a metal coating). Suitable metal substrates can include, but are not limited to, stainless steel, cobalt, titanium, nickel, zirconium, tantalum, chromium, tungsten, molybdenum, manganese, iron, vanadium, niobium, hafnium, aluminum, tin, palladium, ruthenium, iridium, rhodium, gold, silver, platinum, oxides of the foregoing, alloys of the foregoing, and combinations of the foregoing. Suitable methods for forming metallized coatings on substrates include sputtering, thermal evaporation, electron beam evaporation, electroless deposition, and chemical vapor deposition. Suitable polymer substrates can include, but are not limited to, acrylonitrile butadiene styrenes, polyacrylonitriles, polyamides, polycarbonates, polyesters, polyetheretherketones, polyetherimides, polyethylenes, polyethylene terephthalates, polylactic acids, polymethyl methacrylates, polypropylenes, polystyrenes, polyurethanes, polyvinyl chloride, polyvinylidene chlorides, polyethers, polysulfones, silicones, polydimethylsiloxanes, polytetrafluoroethylene, polyisoprenes, and blends and copolymers thereof. In one aspect, the substrate has a surface including a suitable reactive moiety ab initio. Substrates of the invention also include those that have surfaces that have been activated (or modified) to include a reactive moiety. Reactive moieties are useful in that they can be used to covalently bond trihydroxyphenyl groups to the substrate surface, typically via bond formation between a nucleophile on the substrate surface and an unsubstituted carbon of the trihydroxyphenyl group. Such reactive moieties, however, need not be present as the trihydroxyphenyl groups of the compounds will still adsorb to/adhere to/couple to/associate with the substrate in the absence of reactive moieties on the substrate surface.

The substrate according to the invention can be used to provide one or more surfaces of a medical device or medical device component. The medical device or medical device component can be any medical device or medical device component that may benefit from having an active agent immobilized on the surface thereof, particularly medical devices which are in regular contact with the biological fluids of a patient. Medical devices or medical device components can include, but are not limited to, instruments, apparatuses, implements, machines, contrivances, implants, and components and accessories thereof, intended for use in the diagnosis, cure, mitigation, treatment, or prevention of disease or other condition in humans or other animals, or intended to affect the structure or any function of the body of humans or other animals. Exemplary medical devices can include, but are not limited to, extracorporeal blood circuit devices such as hemodialysis and coronary bypass pumps and components thereof. Autotransfusion, apheresis, hemofiltration, plasmapheresis, and extracorporeal membrane oxygenation also involve the use of an extracorporeal blood circuit for removing blood from a patient's circulation and applying a process thereto prior to returning the blood to the patient's circulation.

Specific medical devices and/or medical device components that include substrates that benefit from having an active agent immobilized on the surface thereof include, but are not limited to, tubing; fluid bags; septa; stopcocks; clamps; filters; catheters, such as venous catheters, urinary catheters, Foley catheters, intraurethral catheters, intra-arterial catheters, intraosseous catheters, intrathecal catheters, intra-pulmonary catheters and pain management catheters; tracheal tubes; nasogastric tubes; dialysis sets; dialysis connectors; stents; abdominal plugs; feeding tubes; indwelling devices; surgical tools; needles; cannulae; medical pumps; pump housings; gaskets such as silicone O-rings; syringes; surgical sutures; filtration devices; drug reconstitution devices; implants; metal screws; and metal plates. Additional exemplary medical devices include, but are not limited to, invasive medical devices, durable medical devices, medical fluid containers, medical fluid flow systems, infusion pumps, patient monitors, and any other medical devices which regularly come into contact with a patient's biological fluids.

Examples of durable medical devices include intravenous (I.V.) pumps, patient monitors, and the like. Examples of medical fluid flow systems include I.V. sets, intraperitoneal sets, and components thereof, such as, for example, luer access devices. A typical I.V. set uses plastic tubing to connect a phlebotomized subject to one or more medical fluid sources, such as intravenous solutions or medicament containers. I.V. sets optionally include one or more access devices providing access to the fluid flow path to allow fluid to be added to or withdrawn from the IV tubing. Access devices advantageously eliminate the need to repeatedly phlebotomize the subject and allow for immediate administration of medication or other fluids to the subject, as is well known. Access devices can be designed for use with connecting apparatus employing standard luers, and such devices are commonly referred to as "luer access devices," "luer-activated devices," or "LADs." LADs can be modified with one or more features such as antiseptic indicating devices. Various LADs are illustrated in U.S. Pat. Nos. 5,242,432, 5,360,413, 5,730,418, 5,782,816, 6,039,302, 6,669,681, and 6,682,509, and U.S. Patent Application Publication Nos. 2003/0141477, 2003/0208165, 2008/0021381, and 2008/0021392, the disclosures of which are hereby incorporated by reference in their entireties.

I.V. sets or intraperitoneal sets can incorporate additional optional components including, for example, septa, stoppers, stopcocks, connectors, protective connector caps, connector closures, adaptors, clamps, extension sets, filters, and the like. Thus, additional suitable medical devices and medical device components which may be benefit from the invention include, but are not limited to: I.V. tubing, I.V. fluid bags, I.V. access devices, septa, stopcocks, I.V. set connectors, I.V. set connector caps, I.V. set connector closures, I.V. set adaptors, clamps, I.V. filters, I.V. pumps, I.V. poles, catheters, needles, cannulae, stethoscopes, patient monitors, intraperitoneal tubing, intraperitoneal fluid bags, access devices for intraperitoneal sets, intraperitoneal set connectors, intraperitoneal set adaptors, and intraperitoneal filters. Representative access devices include, but are not limited to: luer access devices including, but not limited to, needleless luer access devices. The surface of the medical device can be any substrate as described herein.

Substrate surfaces can be activated (or modified) to include a reactive moiety by any suitable mechanism known in the art. Suitable reactive moieties on the surface of the substrates of the invention can include, but are not limited to, nucleophilic groups. Nucleophilic groups are well known in the art and can include, but are not limited to, hydroxyl, alkoxides, amines, nitrite, thiol, thiolates, imidazoles, and combinations thereof.

Plasma treatments, including but not limited to, argon or corona treatments, chemical treatments, including but not limited to oxidation treatments, acid treatments, base treatments, and the like can be used to activate or modify a substrate surface to include a reactive moiety. Suitable methods of oxidizing substrate surfaces such that the substrate surface includes a hydroxyl group are known in the art and can include, for example, treatment of the substrate surface with any oxidation agent, including, but not limited to hydrogen peroxide, inorganic peroxides, permanganates, including the potassium, sodium, ammonium, and calcium salts, osmium tetroxide, and combinations of the foregoing. As another example, polyester substrates can be activated or modified to include a hydroxyl group by treating the substrate with an acid treatment, a base treatment, or an argon plasma. Suitable methods to activate or modify the substrate to include an amine include treating a polyamide substrate with an acid treatment, a base treatment, or an argon plasma. Suitable methods to modify the substrate to include a thiol include treating a polythioester substrate with an acid treatment, a base treatment, or an argon plasma. Plasma treatments can be followed by exposing the plasma treated substrate to a gas to generate reactive moieties. For example, plasmas can be used to generate radicals and then followed to generate reactive moieties by exposure to gases such as oxygen, ammonia, and hydrogen sulfide and thereby generate hydroxyl, amine, and thiol, respectively.

Suitable plasmas can be generated from various inert gases and reactive gases, as well as mixtures of inert gases, mixtures of reactive gases, and/or mixtures of inert gases and reactive gases. Plasmas for use in accordance with the present methods can be generated by various known methods, such as by the application of electric and/or magnetic fields. Various types of power sources can be used to generate suitable plasmas for use in the disclosed methods; typical power sources include direct current (DC), radiofrequency (RF), microwave, and laser power sources. A parallel-plate plasma source, for example, uses a RF power source to generate plasma through gas discharge. Another example of an RF power source is an inductive coupling plasma source which uses an inductively coupled RF source to generate plasma. The RF power source can operate at 13.56 MHz or at another suitable frequency readily determined by one of ordinary skill. Microwave power sources include, for example, the electron cyclotron resonance (ECR) source. The microwave frequency can be 2.45 GHz or another suitable frequency readily determined by one of ordinary skill. Plasmas can be generated at various pressures, and suitable plasma pressures can be readily determined by one of ordinary skill. Plasma can be generated, for example, at atmospheric pressure or under vacuum. Damage to the substrate can be more prevalent at higher pressures compared to lower pressures. Thus, the use of lower pressures can prevent or reduce damage to the substrate, thereby allowing increased exposure times and/or increased power levels to be used. Typical pressures at which plasma can be generated include pressures of about 0.001 Torr to about 760 Torr, for example, about 0.01 Torr to about 100 Torr, about 0.05 Torr to about 50 Torr, and/or about 0.1 Torr to about 10 Torr, but higher and lower pressures also can be used.

In a further embodiment of the invention, the substrate surface can be modified to include a radical as a reactive moiety by UV irradiation and/or heat treatment (for example, at about 40 to about 110° C.) of the substrate in the presence of an initiator to create radicals on the surface of the substrate. The initiator can be any initiator known in the art capable of forming a radical when subjected to UV irradiation and/or elevated temperatures, for example, between about 40 and about 110° C. Suitable initiators can include, but are not limited to, benzophenone, peroxides, including but not limited to hydrogen peroxide, benzoyl peroxide, acetyl peroxide, lauryl peroxide, t-butyl peracetate, t-butyl hydroperoxide, and di-t-butyl peroxide, nitrogen dioxide, azobisisobutyronitrile (AIBN), and 2,2-dimethoxy-2-phenylacetophenone (DMPA). As mentioned above, a radical generated on the substrate surface can be converted to reactive moieties such as hydroxyl, amine, and thiol by exposure to gases such as oxygen, ammonia, and hydrogen sulfide, respectively.

Once a substrate surface has been modified to include a reactive moiety such as a hydroxyl, the substrate surface can be further modified such that one reactive moiety is replaced with a different reactive moiety. For example, a thiol can be replaced by a hydroxyl, or vice versa.

The reactive moiety on the substrate surface can be coupled to a compound including a trihydroxyphenyl group. As explained above, the compound including a trihydroxyphenyl group adsorbs to/adheres to/couples to/associates with the substrate surface through covalent bond formation, hydrogen bond formation, ionic bond formation, van der Waals interactions, or combinations of the foregoing; when a reactive moiety is present on the substrate surface, the trihydroxyphenyl group advantageously adsorbs to/adheres to/couples to/associates with the reactive moiety. Typically, the compound including a trihydroxyphenyl group is coupled to the substrate surface by forming one or more covalent bonds with the reactive moieties on the substrate surface through an unsubstituted carbon on the trihydroxyphenyl group or through a reactive group on the trihydroxyphenyl group, as described below. In embodiments wherein the substrate has a metallic substrate surface, without intending to be bound by theory, it is believed that the compound including a trihydroxyphenyl group is chelated to a metal ion of the metallic substrate surface so as to form two or more bonds between the trihydroxyphenyl group and a metal ion of the metallic substrate surface. The compound including a trihydroxyphenyl group is further coupled to an active agent (either before or after coupling of the compound including a trihydroxyphenyl group to the substrate) through an unsubstituted carbon on the trihydroxyphenyl group or through a reactive group on the compound including a trihydroxyphenyl group, ultimately forming a substrate with an active agent immobilized thereto. The compound including a trihydroxyphenyl group adsorbs to/adheres to/couples to/associates with the active agent through covalent bond formation, hydrogen bond formation, ionic bond formation, van der Waals interactions, or combinations of the foregoing. Typically, the compound including a trihydroxyphenyl group is coupled to the active agent by forming one or more covalent bonds with the active agent.

Compound Including a Trihydroxyphenyl Group

The substrate is contacted with a compound including a trihydroxyphenyl group in order to couple the trihydroxyphenyl group to the substrate surface. As previously described, the compound including a trihydroxyphenyl group adsorbs to/adheres to/couples to/associates with the substrate surface through covalent bond formation, hydrogen bond formation, ionic bond formation, van der Waals interactions, or combinations of the foregoing. Typically, when a reactive moiety is present, the trihydroxyphenyl group is coupled to the reactive moiety on the substrate by forming one or more covalent bonds with the reactive moiety. When a metal ion of a metallic surface is present, it is believed that the compound including a trihydroxyphenyl group is coupled to the metallic substrate surface by chelation. The trihydroxyphenyl group therefore, typically has two of the hydroxyls of the trihydroxyphenyl group provided such that they are ortho or meta to one another, i.e., the hydroxyls are provided on directly adjacent carbons of the phenyl right or are provided with one, typically unsubstituted, carbon atom there between. As described above, the compound including a trihydroxyphenyl group encompasses small molecule compounds, polymers including trihydroxyphenyl groups, and trihydroxyphenyl-linker conjugates. The polymers including trihydroxyphenyl groups include polymers wherein the trihydroxyphenyl group is in the polymer backbone as well as polymers including pendant trihydroxyphenyl groups. The trihydroxyphenyl-linker conjugates include small molecule or polymer compounds including a trihydroxyphenyl group coupled to a linker compound.

Generally, suitable trihydroxyphenyl groups have at least two sites of reactivity such that the trihydroxyphenyl group can couple to the substrate, thereby forming a trihydroxyphenyl-treated substrate, and also to at least one of the active agent, another compound including a trihydroxyphenyl group, a linker compound, and/or combinations of the foregoing. Suitable small molecule compounds including a trihydroxyphenyl group include, but are not limited to gallic acid, phloroglucinol carboxylic acid, gallamide, 5-methylbenzene-1,2,3-triol, 3,4,5-trihydroxybenzaldehyde, 2,3,4-trihydroxybenzaldehyde, gallacetophenone, 3,4,5-trihydroxybenzamide, 2,3,4-trihydroxybenzoic acid, 5-hydroxydopamine hydrochloride, methyl gallate, pyrogallol, derivatives thereof and salts of the foregoing. The aforementioned small molecule compounds can also be used to prepare polymers comprising trihydroxyphenyl groups.

As a non-limiting example, gallic acid, through at least the two unsubstituted carbons on its trihydroxyphenyl group phenyl ring, is able to bind to two of a substrate surface reactive moiety, an active agent, another gallic acid, a linker compound, and combinations of the foregoing, thereby immobilizing the active agent on the substrate surface. Gallic acid is also able to bind to a substrate surface reactive moiety, an active agent, another gallic acid, or a linker compound via its carboxylic acid moiety, as described below for a linker compound. Thus, gallic acid advantageously has three hydroxyls as well as three sites of reactivity that may participate in and facilitate the immobilization of an active agent on the substrate surface. Other compounds including a trihydroxyphenyl group necessarily include at least two sites of reactivity, for example, at least two unsubstituted carbons on the phenyl ring and/or reactive groups (such as the aforementioned carboxylic acid moiety) in order to also be able to couple to two of a substrate surface reactive moiety, an active agent, another compound including a trihydroxyphenyl group, a linker compound, and combinations of the foregoing, thereby immobilizing an active agent on the substrate surface. Suitable reactive groups on the phenyl ring of the trihydroxyphenyl group include, but are not limited to, carboxyls, carboxylates, amides, acyl halides, aldehydes, ketones and esters.

Linker Compounds

The compound including a trihydroxyphenyl group can be coupled to a linker compound thereby forming a trihydroxyphenyl-linker conjugate. The compound including a trihydroxyphenyl group adsorbs to/adheres to/couples to/associates with the linker compound through covalent bond formation, hydrogen bond formation, ionic bond formation, van der Waals interactions, or combinations of the foregoing. Typically, the trihydroxyphenyl group is coupled to the linker compound by forming a covalent bond with the linker compound through an unsubstituted carbon on the trihydroxyphenyl group or through a reactive group on the trihydroxyphenyl group. The reactive group on the trihydroxyphenyl group can be any reactive group that can react with a nucleophile on a linker compound. Suitable reactive groups on the trihydroxyphenyl group include, but are not limited to, carboxyls, carboxylates, amides, acyl halides, aldehydes, and esters. The reactive group on the trihydroxyphenyl group can couple to the linker compound, for example, by transesterification or transamidification. The transesterification or transamidification can optionally be promoted by an activator compound such as N,N'-dicyclohexylcarbodiimide (DCC), N,N'-diisopropylcarbodiimide (DIC), hydroxybenzotriazole (HOBt), or 1-hydroxy-7-azabenzotriazole (HOAt). Of course, like the linker compound, an active agent including a nucleophilic group can also couple to the reactive group of the trihydroxyphenyl group by transesterification or transamidification.

The linker compound can be any suitable compound that has a first end group and a second end group that enables the linker to couple to either a reactive group and/or an unsubstituted carbon of the trihydroxyphenyl group and to a polymerizable moiety, so as to form a polymerizable monomer, or to couple to either a reactive group and/or an unsubstituted carbon of the trihydroxyphenyl group and to an active agent so as to form a trihydroxyphenyl-linker-active agent conjugate. Polyethylene glycols, diamines, diols, and dithiols are all useful representative linker compounds. In one aspect, suitable linker compounds include, but are not limited to, compounds according to formula (I):

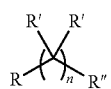

(1)

wherein n is an integer of at least 1, R is any nucleophilic group, including but not limited to hydroxyl, alkoxide, amine, nitrite, thiol, thiolate, imidazole, and amino oxy, R" is R or a reactive group including, but not limited to, carboxyls, carboxylates, amides, acyl halides, aldehydes, and esters, and wherein each R' is the same or different and can be selected from the group consisting of H and substituted or unsubstituted lower alkyl, for example, C1 to about C5 alkyl. When aqueous solutions are used, n is typically about 1 to 5 (as long as solubility is achieved in the selected aqueous system); when organic solvents are used, n can be about 1 to 10. For example, suitable linker compounds can include, but are not limited to, linear bis-amines comprising first and second amine end groups, such as 1,3-diaminopropane, 1,4-diaminobutane, 1,5-diaminopentane, and/or 1,6-diaminohexane.

Suitable linker compounds further include any compound that has two or more terminal functional groups that can couple to either a reactive group and/or an unsubstituted carbon of the trihydroxyphenyl group, a polymerizable moiety, and/or an active agent. As used herein, "terminal" refers to the final functional group of any carbon chain or branch, including, the end groups of linear compounds as well as any branch ends of branched compounds. Typically, the functional groups will be nucleophiles. Nucleophilic groups are well known in the art and can include, but are not limited to, hydroxyl, alkoxide, amine, nitrite, thiol, thiolate, imidazole, aminooxy, and combinations thereof. For example, suitable linker compounds can include, but are not limited to branched polyethylene glycol molecules wherein each branch is terminated with a nucleophilic group (including, but not limited to, 8-Arm PEG-aminooxy, 8-Arm PEG-thiol, 8-Arm PEG-amine, 8-Arm PEG-hydroxyl, 4-Arm PEG-aminooxy, 4-Arm PEG-thiol, 4-Arm PEG-amine, 4-Arm PEG-hydroxyl, and the like), dithiols, bisamines, and other polynucleophiles.

It is believed that upon contacting in solution a compound including a trihydroxyphenyl group and a linker compound, any reactive group(s) and/or unsubstituted carbon(s) on the trihydroxyphenyl group can couple to the linker compound thereby forming a trihydroxyphenyl-linker conjugate. The linker compound adsorbs to/adheres to/couples to/associates with the trihydroxyphenyl group through covalent bond formation, hydrogen bond formation, ionic bond formation, van der Waals interactions, or combinations of the foregoing. Typically the linker compound is coupled to the trihydroxyphenyl group by forming one or more covalent bonds with the trihydroxyphenyl group. Generic trihydroxyphenyl-linker conjugates can be represented by formulae (IIa), (IIb), and (IIc):

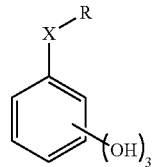

(IIa)

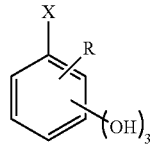

(IIb)

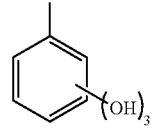

(IIc)

wherein X can be halogen, amine, thiol, aldehyde, carboxylic acid, carboxylate, acyl halide, ester, acrylate, vinyl, C1 to C10 branched or linear alkyl amine, C1 to C10 branched or linear alkyl thiol, C1 to C10 branched or linear alkyl aldehyde, C1 to C10 branched or linear alkyl carboxylic acid, C1 to C10 branched or linear alkyl carboxylate, C1 to C10 branched or linear alkyl acyl halide, C1 to C10 branched or linear alkyl ester, or C1 to C10 branched or linear alkyl acrylate and R is a linker compound. With respect to the length of the carbon chains of the listed substituents, the chain length is typically C1 to C5 when aqueous solutions are used (as long as solubility is achieved in the selected aqueous system); when organic solvents are used, the chain length can be C1 to C10. In accordance with compounds (IIa), (IIb), and (IIc) the three hydroxyl groups can be provided on any three of $C_2$, $C_3$, $C_4$, $C_5$, and $C_6$. For example, when the compound including a trihydroxyphenyl group is carboxylic acid such as gallic acid (and thus X is carboxyl), the trihydroxyphenyl-linker conjugate can be of formula (IIa) or formula (IIb):

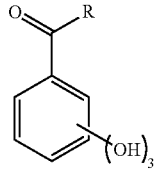

(IIa)

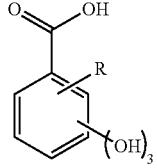

(IIb)

wherein, as above, R is the linker compound. Further, when the trihydroxyphenyl-linker conjugate is a gallic acid-linker conjugate according to (IIa) and (IIb), the three hydroxyl groups are provided on $C_3$, $C_4$, and $C_5$, and the linker, R, is provided on the carboxyl group (IIa) or one of $C_2$ or $C_6$ (IIb). When the compound including a trihydroxyphenyl group is pyrogallol, the pyrogallol-linker conjugate can be of formula (IIc):

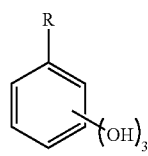
(IIc)

wherein R is the linker compound and the three hydroxyl groups can be provided on any consecutive three of $C_2$, $C_3$, $C_4$, $C_5$, and $C_6$.

The linker compound can be coupled to a compound including a trihydroxyphenyl group prior to contacting a substrate with the compound including a trihydroxyphenyl group. Alternatively, a trihydroxyphenyl-treated substrate may be contacted with a solution of linker compound, thereby coupling the linker compound to the trihydroxyphenyl group. The linker end group that is distal from the trihydroxyphenyl group can couple to an active agent, thereby forming a trihydroxyphenyl-linker-active agent conjugate, or to a polymerizable moiety, so as to form a polymerizable monomer.

Polymerizable Monomers/Polymers Having Pendant Trihydroxyphenyl Groups

In embodiments wherein the compound including a trihydroxyphenyl group is a polymer, the polymer can include at least one monomer having a pendant trihydroxyphenyl group. A polymer having a pendant trihydroxyphenyl group can be polymerized from polymerizable monomers prepared from a small molecule compound including a trihydroxyphenyl group that has been modified to include a linker compound that includes a polymerizable moiety.

The polymerizable monomer can be formed by coupling a polymerizable moiety to a trihydroxyphenyl-linker conjugate. The trihydroxyphenyl-linker conjugate includes a linker end group distal from the trihydroxyphenyl group. The distal end group of the linker can form a covalent bond with a polymerizable moiety.

In general, the polymerizable moiety can be any functional group that includes a polymerizable α,β unsaturated end group. Suitable polymerizable moieties include, but are not limited to, acrylate, methacrylate, acrylamide, methacrylamide, vinyl acetate, and esters of the foregoing. The covalent bond between the linker compound and the polymerizable moiety may be formed by transesterification or transamidification and may be promoted by an activator compound such as N,N'-dicyclohexylcarbodiimide (DCC), N,N'-diisopropylcarbodiimide (DIC), hydroxybenzotriazole (HOBt), or 1-hydroxy-7-azabenzotriazole (HOAt).

In some embodiments, a polymerizable monomer including a trihydroxyphenyl group can also be formed by coupling a reactive group and/or unsubstituted carbon of the phenyl ring of the trihydroxyphenyl group with a linker compound having a first end group and a second end group, wherein the first end group is a nucleophilic group and the second end group is a polymerizable α,β unsaturated end group. Suitable linker compounds of this embodiment include, but are not limited to, 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 6-hydroxyhexyl acrylate, 6-hydroxyhexyl methacrylate, N-(3-hydroxy-propyl)methacrylamide, N-(4-hydroxybutyl)acrylamide, N-(4-hydroxybutyl)methacrylamide, N-(6-hydroxyhexyl)-acrylamide, N-(6-hydroxyhexyl)methacrylamide, N-methyl-N-(2-hydroxyethyl)acrylamide, N-methyl-N-(2-hydroxyethyl)methacrylamide, N-methyl-N-(3-hydroxypropyl)acrylamide, N-methyl-N-(3-hydroxypropyl)methacrylamide, N-methyl-N-(4-hydroxybutyl)acrylamide, N-methyl-N-(4-hydroxybutyl)methacrylamide, N-methyl-N-(6-hydroxyhexyl)acrylamide, N-methyl-N-(6-hydroxyhexyl)methacrylamide, and 4-aminobutylacrylamide. Generally, suitable linker compounds of this embodiment can include, but are not limited to, compounds according to formula (III):

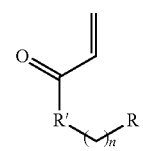
(III)

wherein n is 0 or an integer of at least 1, R is any nucleophilic group, including but not limited to hydroxyl, alkoxide, amine, nitrite, thiol, and thiolate, and R' can be selected from the group consisting of oxygen, NR", and CR$_2$", and each R" can be the same or different and can be selected from the group consisting of H, and substituted or unsubstituted lower alkyl, for example C1 to about C5 alkyl.

Generic polymerizable monomers including a trihydroxyphenyl group are represented by formula (IVa), (IVb), and (IVc):

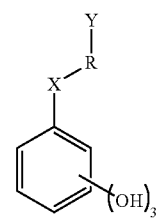
(IVa)

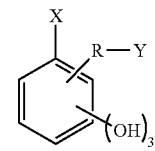
(IVb)

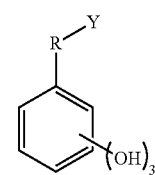
(IVc)

wherein X can be halogen, amine, thiol, aldehyde, carboxylic acid, carboxylate, acyl halide, ester, acrylate, vinyl, C1 to C10 branched or linear alkyl amine, C1 to C10 branched or linear alkyl thiol, C1 to C10 branched or linear alkyl aldehyde, C1 to C10 branched or linear alkyl carboxylic acid, C1 to C10 branched or linear alkyl carboxylate, C1 to C10 branched or linear alkyl acyl halide, C1 to C10 branched or linear alkyl ester, or C1 to C10 branched or linear alkyl acrylate, Y can be a polymerizable moiety such as acrylate, methacrylate, acrylamide, methacrylamide, vinyl acetate, and esters of the foregoing, and R is a linker compound. With respect to the length of the carbon chains of the listed substituents, the chain length is typically C1 to C5 when aqueous solutions are used (as long as solubility is achieved in the selected aqueous system); when organic solvents are used, the chain length can be C1 to C10. In accordance with compounds (IVa), (IVb), and (IVc) the three hydroxyl groups can be provided on any three of $C_2$, $C_3$, $C_4$, $C_5$, and $C_6$. For example, when the compound including a trihydroxyphenyl group is a carboxylic acid such as gallic acid (and thus X is carboxyl), the polymerizable monomer including a trihydroxyphenyl group can be of formula (IIa) or formula (IIb):

(IVa)

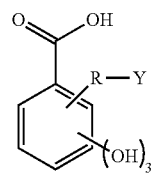

(IVb)

wherein R is the linker compound, and Y is the polymerizable moiety. Further, when the compound including a trihydroxyphenyl group is gallic acid, the polymerizable monomer according to (IVa) and (IVb) comprises the three hydroxyl groups on $C_3$, $C_4$, and $C_5$, and the linker, R, is provided on the carboxyl group (IVa) or one of $C_2$ or $C_6$ (IVb). When the compound including a trihydroxyphenyl group is pyrogallol, the polymerizable monomer can be of formula (IVc):

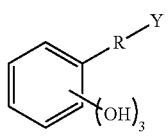

(IVc)

wherein R is the linker compound, Y is the polymerizable moiety, and the three hydroxyl groups can be provided on any consecutive three of $C_2$, $C_3$, $C_4$, $C_5$, and $C_6$.

The polymerizable monomer including a trihydroxyphenyl group is polymerized to form a homopolymer or is copolymerized with one or more secondary polymerizable monomers (including polymerizable groups) to form a polymer containing at least one monomer having a pendant trihydroxyphenyl group. Copolymers containing pendant trihydroxyphenyl groups and one or more secondary polymerizable monomers can be polymerized to form random copolymers and/or block copolymers, as is known in the art. Suitable secondary polymerizable monomers can be any monomer comprising a polymerizable moiety. Secondary polymerizable monomers may have a pendant nucleophile (i.e., a nucleophile that will be pendant from the monomer after polymerization), such as an amine, hydroxyl, or thiol, such that when the secondary monomer is incorporated into the polymer containing at least one monomer having a pendant trihydroxyphenyl group, the pendant nucleophile can facilitate coupling to the substrate, and thereby formation of the trihydroxyphenyl-treated substrate. Secondary polymerizable monomers may alternatively have a pendant reactive group (i.e., a reactive group that will be pendant from the monomer after polymerization), including but not limited to N-hydroxysuccinimide, succinimide, and the like, such that when the secondary monomer is incorporated into the polymer containing at least one monomer having a pendant trihydroxyphenyl group the pendant reactive group can couple to the active agent, thereby forming an active agent-trihydroxyphenyl conjugate, or the pendant reactive group can couple to the substrate, thereby forming a trihydroxyphenyl-treated substrate.

Suitable radical initiators for initiating polymerization of the polymerizable monomer having the trihydroxyphenyl group, and optionally a secondary monomer, include, but are not limited to, azo compounds, organic peroxides, and combinations thereof. Suitable azo compounds include, but are not limited to, azobisisobutyronitrile (AIBN), and 1,1-azobis(cyclohexanecarbonitrile) (ABCN). Suitable organic peroxides include, but are not limited to, cyclic peroxides, diacyl peroxides, dialkyl peroxides, hydroperoxides, peroxycarbonates, peroxydicarbonates, peroxyesters, and peroxyketals. Suitable cyclic peroxides include, but are not limited to, 3,6,9-triethyl-3,6,9-trimethyl-1,4,7-triperoxonane. Suitable diacyl peroxides include, but are not limited to, di(3,5,5-trimethylhexanoyl) peroxide. Suitable dialkyl peroxides include, but are not limited to, 2,5-dimethyl-2,5-di(tert-butylperoxy)hexane; 2,5-dimethyl-2,5-di(tert-butylperoxy)hexyne-3; di-tert-amyl peroxide; di-tert-butyl peroxide; and tert-butyl cumyl peroxide. Suitable hydroperoxides include, but are not limited to, tert-Amyl hydroperoxide; and 1,1,3,3-tetramethylbutyl hydroperoxide. Suitable peroxycarbonates include, but are not limited to, tert-butylperoxy 2-ethylhexyl carbonate; tert-amylperoxy 2-ethylhexyl carbonate; and tert-butylperoxy isopropyl carbonate. Suitable peroxydicarbonates include, but are not limited to, di(2-ethylhexyl) peroxydicarbonates; and di-sec-butyl peroxydicarbonates. Suitable peroxyesters include, but are not limited to, test-amyl peroxy-2-ethylhexanoate; tert-amyl peroxyneodecanoate; tert-amyl peroxypivalate; tert-amyl peroxybenzoate; tert-amyl peroxyacetate; 2,5-dimethyl-2,5-di(2-ethylhexanoylperoxy)hexane; tert-butyl peroxy-2-ethylhexanoate; tert-butyl peroxyneodecanoate; tert-butyl peroxyneoheptanoate; tert-butyl peroxypivalate tert-butyl, peroxydiethylacetate; tert-butyl peroxyisobutyrate; 1,1,3,3-tetramethylbutyl peroxy-2-ethylhexanoate; 1,1,3,3-tetramethylbutyl peroxyneodecanoate; 1,1,3,3-tetramethylbutyl peroxypivalate; tort-butyl peroxy-3,5,5-trimethylhexanoate; cumyl peroxyneodecanoate; tert-butyl peroxybenzoate; and tert-butyl peroxyacetate. Suitable peroxyketals include, but are not limited to, 1,1-di(tert-amylperoxy)cyclohexane; 1,2-di(tert-butylperoxy)cyclohexane; 1,1-di(tert-butylperoxy)-3,3,5-trimethylcyclohexane; and 2,2-di(tert-butylperoxy)butane.

Ranges may be expressed herein as from "about" or "approximately" one particular value and/or to "about" or "approximately" another particular value. When such a range is expressed, another embodiment according to the invention includes from the one particular value and/or to the other particular value. Similarly, when particular values are expressed as approximations, but use of antecedents such as "about," "at least about," or "less than about," it will be understood that the particular value forms another embodiment.

The optional secondary monomer can be included in a copolymer with the monomer having the trihydroxyphenyl group in an amount of up to about 95 mol %, for example, about 0.5 to about 95 mol %, about 0.5 to about 90 mol %, about 1 to about 90 mol %, about 1 to about 85 mol %, about 5 to about 85 mol %, about 5 to about 80 mol %, about 10 to about 80 mol %, about 10 to about 75 mol %, about 15 to about 75 mol %, about 5 to about 70 mol %, about 10 to about 70 mol %, about 15 to about 70 mol %, about 15 to about 65 mol %, about 20 to about 65 mol %, about 20 to about 60 mol %, about 25 to about 60 mol %, about 25 to about 55 mol %, about 30 to about 55 mol %, about 30 to about 50 mol %, about 35 to about 50 mol %, about 35 to about 45 mol %, and/or about 35 to about 40 mol %.

Polymers containing a pendant trihydroxyphenyl group can be terminated with a reactive group through which an active agent can couple to the polymer. The reactive group can be any reactive group as previously described herein, including, but not limited to, carboxyls, carboxylates, amides, acyl halides, aldehydes, and esters. The reactive group can be included in a compound that can act as a chain transfer agent in polymerizations. Suitable chain transfer agents with reactive groups can include, but are not limited to 3-mercaptopropionic acid, isooctyl 3-mercaptopropionate, and combinations of the foregoing. Alternatively, the active agent will couple to the polymer through an unsubstituted carbon on the pendent trihydroxyphenyl groups and, therefore, the chain end of the polymer need not be able to couple to the active agent.

As described above, compounds including a trihydroxyphenyl group that are polymers containing at least one monomer having a pendant trihydroxyphenyl group can be coupled to a further linker compound, thereby forming a trihydroxyphenyl-linker conjugate that can couple to an active agent. The linker compound adsorbs to/adheres/couples to/associates with the trihydroxyphenyl group through covalent bond formation, hydrogen bond formation, ionic bond formation, van der Waals interactions, or combinations of the foregoing. Typically, the linker compound is coupled to the trihydroxyphenyl group by forming one or more covalent bonds with the unsubstituted carbons of the trihydroxyphenyl group.

Polymers Having Trihydroxyphenyl Groups in the Backbone

In alternative embodiments wherein the compound including a trihydroxyphenyl group is a polymer, the trihydroxyphenyl group can be in the backbone of the polymer. A polymer having the trihydroxyphenyl groups in the backbone can be polymerized from a small molecule compound including a trihydroxyphenyl group that has at least two sites of reactivity. Without intending to be bound by any particular theory, it is believed that, the small molecule compounds including a trihydroxyphenyl group can self polymerize from a quinone-like species, shown below, by the formation of covalent bonds between unsubstituted carbon atoms in the phenyl rings of two or more adjacent trihydroxyphenyl groups.

The trihydroxyphenyl groups of the compounds including a trihydroxyphenyl group of the invention are generally considered to be in a pH dependent equilibrium with a quinone-like species when in solution. For example, the equilibrium between gallic acid (Compound A) and the quinone-like species (Compound B) is shown below. It is believed that the equilibrium favors the trihydroxylated species, Compound A, at a more acidic pH.

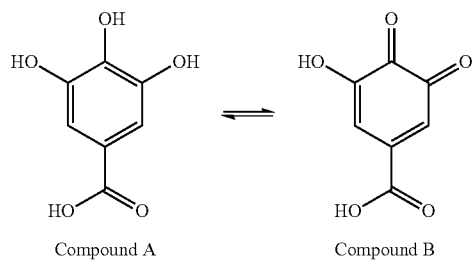 [SMILES: O=C(O)c1cc(O)c(O)c(O)c1 ; O=C(O)C1=CC(=O)C(=O)C(O)=C1]

Compound A     Compound B

After the compound including a trihydroxyphenyl group has come into contact with the substrate surface, the trihydroxyphenyl group can covalently bind or otherwise couple to a reactive moiety presented by/on the substrate surface through an unsubstituted carbon of the phenyl ring of the trihydroxyphenyl group, thereby forming a trihydroxyphenyl-treated substrate. Alternatively, after the compound including a trihydroxyphenyl group has come into contact with a metallic substrate surface, the trihydroxyphenyl group can chelate or otherwise couple to the substrate surface through one or more available hydroxyl groups on the trihydroxyphenyl ring, thereby forming a trihydroxyphenyl-treated substrate.

The small molecule compound including a trihydroxyphenyl group can also self polymerize in situ to form polymers containing repeat units of the trihydroxyphenyl group in the polymer backbone. Without intending to be bound by any particular theory, it is believed that, the trihydroxyphenyl group can self polymerize from the quinone-like species by the formation of covalent bonds between unsubstituted carbon atoms in the phenyl rings of two or more adjacent trihydroxyphenyl groups. Thus, in one embodiment, the unsubstituted carbon of the phenyl ring to which an active agent can couple can be the terminal trihydroxyphenyl group of a polymer chain that is coupled to the substrate surface. Further, when the compound including a trihydroxyphenyl group is a polymer including pendant trihydroxyphenyl groups, it is believed that the unsubstituted carbons of the phenyl rings of the pendant trihydroxyphenyl groups can internally cross-link if in close proximity with other pendant trihydroxyphenyl groups on the polymer chain or can cross-link multiple polymer chains.

Active Agents

The active agent can include, but is not limited to antimicrobial agents, such as antibacterial agents, antifouling agents, anti-inflammatory agents, such as complement inhibitors, including but not limited to C1 inhibitors, e.g., eculizumab, and C5 inhibitors, antithrombogenic agents, such as anticoagulating agents, and combinations thereof. For example, the active agent can include, but is not limited to, chitosan, dextran, linear polyethylene glycol (PEG), looped polyethylene glycol (PEG), polyethylene glycol derivatives including, but not limited to thiol-terminated PEG, N-hydroxysuccinimide (NHS)-terminated PEG and amine-terminated PEG, poly(N-vinylpyrrolidone)(PVP) and PVP derivatives including, but not limited to, thiol-terminated PVP, amine-terminated PVP, and carboxyl-terminated PVP, heparin, including but not limited to, fractionated heparin, unfractionated heparin, and heparin derivatives, said heparin derivatives including but not limited to, enoxaparin, dalteparin, and tinzaparin, quaternary ammonium polymers, albumin, polyethylenimine, 4-hydroxycoumarin derivatives such as warfarin, coumatetralyl, phenprocoumon, acenocoumarol, dicoumarol, tioclomarol, and brodifacoum, and combinations of the foregoing. In embodiments comprising polyethylene glycol, chitosan, or heparin, the molecular weight can be in a range of about 500 Da to about 1,000,000 Da, about 1000 Da to about 500,000 Da, about 2000 Da to about 500,000 Da, about 2000 Da to about 250,000 Da, and/or about 2000 Da to about 100,000 Da. In general, the active agent includes a functional group. Suitable functional groups include, but are not limited to, nucleophilic groups. Nucleophilic groups are well known in the art and can include, but are not limited to, hydroxyl, alkoxide, amine, nitrite, thiol, thiolate, imidazole, and combinations thereof. Nucleophilic groups on chitosan include amine and hydroxyl groups; nucleophilic groups on PEG and/or PEG derivatives include hydroxyl groups, thiol groups, amine groups; nucleophilic groups on PVP derivatives include carboxyl groups, thiol groups, amine groups; nucleophilic groups on heparin and heparin derivatives include hydroxyl, carboxylate, and sulfate. The thiol, amine, and carboxyl-terminated PVP derivatives can be prepared by terminating PVP polymerization with an appropriate chain transfer agent such as, for example, mercaptoacetic acid or mercaptoethylamine, or by further derivitizing a carboxyl-terminated PVP such as, for example, by reacting the carboxyl-terminated PVP with cysteamine followed by a reducing agent such as tris(2-carboxyethyl)phosphine (TCEP) or dithiothreitol (DTT).

Coupling of a Compound Including a Trihydroxyphenyl Group and a Substrate

In one embodiment of the invention, the compound including a trihydroxyphenyl group is coupled to a substrate surface by contacting the substrate with a solution of the compound including a trihydroxyphenyl group. The substrate can be completely immersed in the solution of the compound including a trihydroxyphenyl group, for example, by dip coating. Alternatively, a solution of the compound including a trihydroxyphenyl group can be sprayed or cast onto the substrate, for example, by spin casting or spraying a solution such as an aerosolized solution. For substrates having an interior lumen, such as tubing, the solution can be flowed into the lumen to coat the interior thereof. The solvent can be any solvent that is capable of serving as a carrier for the compound including a trihydroxyphenyl group. For example, most frequently water is used, but organic solvents including but not limited to alcohols, diols, organosulfurs such as sulfolane, ethers, such as diethyl ether and tetrahydrofuran, alkanes, aromatics, halocarbons, such as chloroform and dichloromethane, and combinations of the foregoing can be used. In embodiments of the methods disclosed herein, the solution comprising the compound including a trihydroxyphenyl group is at a pH in a range of about 7.5 to about 9.5, about 8 to about 9, and/or about 8.5 so the equilibrium is not biased toward either direction of the equilibrium as mentioned above. The solution of the compound including a trihydroxyphenyl group may further include a buffer in order to maintain the pH within the foregoing ranges, including, but not limited to, N,N-bis(2-hydroxyethyl)glycine (Bicine), 3-1 {[tris(hydroxymethyl)methyl]amino}propanesulfonic acid (TAPS), tris(hydroxymethyl)methylamine (Tris), and N-tris(hydroxymethyl)methylglycine (Tricine). Of course, one or more of carbonate, phosphate and other known buffer systems for maintaining relatively high pH values can also be used.

The concentration of the compound including a trihydroxyphenyl group in the solution of the compound including a trihydroxyphenyl group can generally be any concentration. The concentration is typically chosen such that the compound including a trihydroxyphenyl group is fully soluble in a chosen solvent, without forming a saturated solution of the compound including a trihydroxyphenyl group. Further, because the trihydroxyphenyl group can self-polymerize in situ, the concentration of the compound including a trihydroxyphenyl group is typically selected such that the compound including a trihydroxyphenyl group will be provided to the substrate at an acceptable rate, desirably without excessive self-polymerization or cross-linking, and therefore gelling, of the solution. Exemplary concentrations of compounds including a trihydroxyphenyl groups in solution can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, and/or about 0.05 to about 5 mg/ml, for example, about 1 mg/ml, and/or about 5 mg/ml.

The substrate can be contacted with and/or immersed in the solution of the compound including a trihydroxyphenyl group for any duration of time suitable for coupling the compound including a trihydroxyphenyl group to the substrate. For example, the substrate can be contacted with and/or immersed in the solution of the compound including a trihydroxyphenyl group for any duration of time suitable for forming one or more covalent bonds between a reactive moiety on the substrate (when present) and the compound including a trihydroxyphenyl group. Alternatively, the substrate can be contacted with and/or immersed in the solution of the compound including a trihydroxyphenyl group for any duration of time suitable for chelating a metal ion of a metallic substrate (when present) and the compound including a trihydroxyphenyl group. The rate of the coupling of the compound including a trihydroxyphenyl group on the substrate can depend, in part, on the concentration of the compound including a trihydroxyphenyl group in the compound including a trihydroxyphenyl group solution, the substrate surface to solution volume ratio, the ionic strength of the solution, the pH of the solution, and the temperature. The duration of contact of the substrate with the solution of compound including a trihydroxyphenyl group can be varied for any suitable time period for coupling the compound including the trihydroxyphenyl group to the substrate, for example, when using dip coating, for example, about 10 seconds to about 24 hours. When the duration of contact of the substrate with the solution of the compound including a trihydroxyphenyl group increases above 24 hours (and one of the foregoing exemplary concentrations of the compound including a trihydroxyphenyl group is used), little difference in the amount of compound including a trihydroxyphenyl group coupled to the substrate is expected (relative to a 24 hour exposure time). Without intending to be bound by theory, while it is believed that after 24 hours the compound including the trihydroxyphenyl group may continue to be coupled to the substrate, it is expected that the amount of the compound including the trihydroxyphenyl group provided after 24 hours will have little effect on the amount of active agent that is ultimately immobilized on the substrate surface, and further, it is believed that the likelihood of the compound including a trihydroxyphenyl group self-polymerizing or cross-linking in solution, even at low concentrations, increases with time.

In embodiments of the invention where the compound including a trihydroxyphenyl group comprises a trihydroxyphenyl-linker conjugate, a trihydroxyphenyl-linker conjugate is initially formed by coupling the trihydroxyphenyl group of a small molecule or polymer compound including a trihydroxyphenyl group with a nucleophile on a linker compound via an unsubstituted carbon or reactive group on the phenyl ring of the trihydroxyphenyl group, and is typically followed by contacting the substrate with a solution of the trihydroxyphenyl-linker conjugate. The trihydroxyphenyl-linker conjugate can be formed by combining in solution a compound including a trihydroxyphenyl group and a linker compound. The solution of the compound including a trihydroxyphenyl group and/or the linker compound can be prepared in any solvent capable of acting as a carrier for the compound including a trihydroxyphenyl group and/or the linker compound. For example, most frequently water is used, but other solvents including but not limited to, alcohols, diols, organosulfurs such as sulfolane, ethers, such as diethyl ether and tetrahydrofuran, alkanes, aromatics, halocarbons, such as chloroform and dichloromethane, and combinations of the foregoing can also be used.

In refinements of the aforementioned embodiment, the solutions of compounds including a trihydroxyphenyl group and linker compounds are maintained at a pH in a range of about 7.5 to about 9.5, or about 8 to about 9, or about 8.5. The solution of compound including a trihydroxyphenyl group and/or solution of linker compound may further include a buffer in order to maintain the pH within the foregoing ranges, including, but not limited to, N,N-bis(2-hydroxyethyl)glycine (Bicine), 3-{[tris(hydroxymethyl)methyl]amino}propanesulfonic acid (TAPS), tris(hydroxymethyl)methylamine (Tris), and N-tris(hydroxymethyl)methylglycine (Tricine). Of course, one or more of carbonate, phosphate and other known buffer systems can also be used.

The concentrations of the compound including a trihydroxyphenyl group and linker compound in solution can be any concentration. The concentrations are typically chosen such that the compound including a trihydroxyphenyl group and/or linker compound are fully soluble in a chosen solvent, without forming saturated solutions. Exemplary compound including a trihydroxyphenyl group and/or linker compound concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml and/or about 3 mg/ml. The ratio of compound including a trihydroxyphenyl group to linker compound can be in a range of about 1:8 to about 8:1, about 1:7 to about 7:1, about 1:6 to about 6:1, about 1:5 to about 5:1, about 1:4 to about 4:1, about 1:3 to about 3:1, and/or about 1:2 to about 2:1, for example about 1:1.

The trihydroxyphenyl-linker conjugate can be coupled to the substrate by contacting the substrate with a solution of trihydroxyphenyl-linker conjugate. The substrate can be completely immersed in the solution of the trihydroxyphenyl-linker conjugate, for example, by dip coating. Alternatively, a solution of the trihydroxyphenyl-linker conjugate can be sprayed or cast onto the substrate, for example, by spin casting or spraying a solution such as an aerosolized solution. For substrates having an interior lumen, such as tubing, the solution can be flowed into the lumen to coat the interior thereof.

The concentration of the trihydroxyphenyl-linker conjugate in the trihydroxyphenyl-linker conjugate solution can be any concentration. The concentration of the trihydroxyphenyl-linker conjugate is typically chosen such that the trihydroxyphenyl-linker conjugate is fully soluble in a chosen solvent, without forming a saturated solution. Exemplary trihydroxyphenyl-linker conjugate concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml or about 3 mg/ml.

The substrate can be contacted with and/or immersed in the solution of the trihydroxyphenyl-linker conjugate for any duration suitable to couple the trihydroxyphenyl-linker conjugate to the substrate. It is believed that the trihydroxyphenyl-linker conjugate can couple to the substrate through either one or both of the end group of the linker compound distal from the trihydroxyphenyl group and any residual reactive groups on the trihydroxyphenyl group. For example, in embodiments of the invention the duration of contact can be any duration of time suitable for forming a covalent bond between one or more of the linker or trihydroxyphenyl group with a reactive moiety (when present) on the substrate surface. The rate of the coupling of the trihydroxyphenyl-linker conjugate and the substrate can depend, in part, on the concentration of the trihydroxyphenyl-linker conjugate solution thereof, the substrate surface to solution volume ratio, the ionic strength of the solution, the pH of the solution, and the temperature. The duration of contact of the substrate with the solution of trihydroxyphenyl-linker conjugate can be varied for any suitable time period for coupling the trihydroxyphenyl-linker conjugate to the substrate, for example, when using dip coating, from about 10 seconds to about 24 hours. When the duration of contact of the substrate with the solution of trihydroxyphenyl-linker conjugate increases above 24 hours (and one of the foregoing exemplary concentrations of trihydroxyphenyl-linker conjugate is used), little difference in the amount of trihydroxyphenyl-linker conjugate coupled to the substrate surface is expected (relative to a 24 hour exposure time). Without intending to be bound by theory it is believed that while the trihydroxyphenyl-linker conjugate may continue to be coupled to the substrate after 24 hours, it is expected that the amount of the trihydroxyphenyl-linker conjugate provided after 24 hours will have little effect on the amount of active agent that is ultimately immobilized on the substrate surface, and further, it is believed that the likelihood of the trihydroxyphenyl group self-polymerizing or cross-linking, and therefore gelling of the solution, even at low concentrations, increases with time.

Coupling of a Trihydroxyphenyl-treated Substrate and an Active Agent

It is believed that, upon exposure of the trihydroxyphenyl-treated substrate to an active agent, any sites of reactivity available on the trihydroxyphenyl group (i.e., reactive groups and/or unsubstituted carbons on the phenyl ring), or linker compound thereon, can couple to the active agent, thereby immobilizing the active agent on the substrate surface. The active agent adsorbs to/adheres to/couples to/associates with the trihydroxyphenyl group through covalent bond formation, hydrogen bond formation, ionic bond formation, van der Waals interactions, or combinations of the foregoing. Typically, the active agent is coupled to the compound including a trihydroxyphenyl group by forming one or more covalent bonds with an unsubstituted carbon on the trihydroxyphenyl group or through a reactive group on the trihydroxyphenyl group. The reactive group on the trihydroxyphenyl group can be any reactive group that can react with a nucleophile on an active agent. Suitable reactive groups on the trihydroxyphenyl group include, but are not limited to, carboxyls, carboxylates, amides, acyl halides, aldehydes, and esters. The reactive group on the trihydroxyphenyl group can couple to the linker compound, for example, by transesterification or transamidification. The transesterification or transamidification can optionally be promoted by an activator compound such as N,N'-dicyclohexylcarbodiimide (DCC), N,N'-diisopropylcarbodiimide (DIC), hydroxybenzotriazole (HOBt), or 1-hydroxy-7-azabenzotriazole (HOAt). In embodiments wherein a covalent bond forms between the active agent and an unsubstituted carbon of the phenyl ring of the trihydroxyphenyl group, it is believed the covalent bond may be formed by Michael addition. For example, the active agent chitosan can couple to a trihydroxyphenyl group through a hydroxyl or amine group on the active agent that covalently binds with an unsubstituted carbon on the phenyl ring of the trihydroxyphenyl group. Other suitable active agents necessarily include a similar nucleophilic group and therefore can also couple to the compound including a trihydroxyphenyl group in a similar fashion as chitosan.

In one embodiment of the invention, the active agent is coupled to the trihydroxyphenyl-treated substrate surface by contacting the trihydroxyphenyl-treated substrate surface with an active agent. The active agent can be provided in solution or, if the active agent is a liquid, the active agent can be provided neat. The trihydroxyphenyl-treated substrate can be completely immersed in the active agent or solution of the active agent, for example, by dip coating. Alternatively, the active agent or a solution of active agent can be sprayed or cast onto the trihydroxyphenyl-treated substrate, for example, by spin casting or spraying a solution such as an aerosolized solution. For substrates having an interior lumen, such as tubing, the solution can be flowed into the lumen to coat the interior thereof.

The active agent solution solvent can be any solvent that is capable of serving as a carrier for the active agent. For example, most frequently water is used, but organic solvents including but not limited to, alcohols, diols, organosulfurs such as sulfolane, ethers such as diethyl ether and tetrahydrofuran, alkanes, aromatics, halocarbons such as chloroform and dichloromethane, and combinations of the foregoing can also be used. In one embodiment of the methods disclosed herein, the solution of active agent is at a pH in a range of about 5.5 to about 8.5, or about 6 to about 8, or about 7.5, when coupling the active agent to a trihydroxyphenyl group or a linker compound. The solution of the active agent may further include a buffer in order to maintain the pH within the foregoing ranges as is well known in the art. Suitable buffers for maintaining such a pH, include, but are not limited to, N,N-bis(2-hydroxyethyl)glycine (Bicine), 3-{[tris(hydroxymethyl)methyl]amino}propanesulfonic acid (TAPS), tris(hydroxymethyl)methylamine (Tris), 4-2-hydroxyethyl-1-piperazineethanesulfonic acid (HEPES), and N-tris(hydroxymethyl)methylglycine (Tricine). Of course, one or more of carbonate, phosphate and other known buffer systems for maintaining relatively higher pH values can also be used.

In alternative embodiments, the trihydroxyphenyl-treated substrate can be contacted with solutions of active agents having a lower pH. For example, the solution of active agent can be maintained at a pH in a range of about 4 to about 5.5, for example, about 4.0, about 4.1, about 4.2, about 4.3, about 4.4, about 4.5, about 4.6, about 4.7, about 4.8, about 4.9, about 5, about 5.1, about 5.2, about 5.3, about 5.4, and/or about 5.5, when coupling the active agent to a trihydroxyphenyl group or a linker compound. Suitable active agents for coupling at lower pH include, but are not limited to, heparin and chitosan. The solution of the active agent may further include a buffer in order to maintain the pH within the foregoing ranges as is well known in the art. Suitable buffers for maintaining such a pH include one or more of acetate, citrate, lactate, phosphate and other known buffer systems can also be used.

The concentration of the active agent in the active agent solution can generally be any concentration. The concentration of the active agent is typically chosen such that the active agent is fully soluble in a chosen solvent, without forming a saturated active agent solution. Higher concentrations are generally preferred to reduce the time needed to couple the active agent to the trihydroxyphenyl group. Exemplary active agent concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml or about 3 mg/ml.

The trihydroxyphenyl-treated substrate can be contacted with and/or immersed in the active agent or solution of active agent for any duration of time suitable to couple the active agent and the trihydroxyphenyl group of the trihydroxyphenyl-treated substrate. The rate of the coupling of the active agent to the trihydroxyphenyl-treated substrate can depend, in part, on the concentration of the active agent in the active agent solution, the substrate surface to solution volume ratio, the ionic strength of the solution, and the temperature. The duration of contact of the trihydroxyphenyl-treated substrate with the active agent or solution of active agent can be varied for any suitable time period for providing a layer on a substrate, for example when using dip coating from about 10 seconds to about 24 hours. When the duration of contact of the trihydroxyphenyl-treated substrate with the solution of active agent increases above 24 hours (and one of the foregoing exemplary concentrations of active agent is used), little difference in the amount of active agent immobilized to the substrate surface is expected (relative to a 24 hour exposure time). Without intending to be bound by theory, while it is believed that the active agent may continue to be immobilized on the trihydroxyphenyl-treated substrate, it is expected that the amount of the active agent immobilized after 24 hours will have little effect on the activity (antibacterial, antimicrobial, etc.) of the resulting substrate having an active agent immobilized thereto.

In embodiments of the invention where the compound including a trihydroxyphenyl group comprises a trihydroxyphenyl-linker conjugate, the active agent can adsorb to/adhere to/couple to/associate with a linker coupled to the trihydroxyphenyl group through covalent bond formation, hydrogen bond formation, ionic bond formation, van der Waals interactions, or combinations of the foregoing. Typically, the active agent is coupled to the linker that is coupled to a trihydroxyphenyl group by forming one or more covalent bonds with the end group of the linker compound distal from the trihydroxyphenyl group. When the group of the linker compound that will couple to the active agent is a reactive group including, but not limited to, carboxyl, carboxylate, amide, acyl halides, aldehydes, and esters, it is believed that the linker is coupled to the active agent through the reactive group on the linker and a nucleophilic group on the active agent. It is further believed that when the end group of the linker that will couple to the active agent is a nucleophile such as hydroxyl, alkoxide, amine, nitrite, thiol, and thiolate, the linker can couple to an active agent, including but not limited to heparin, chitosan, quaternary chitosan, etc.

As described above, "active agent" encompasses active agent-linker conjugates. In embodiments of the invention where the active agent comprises an active agent-linker conjugate, an active agent-linker conjugate is initially formed by coupling a nucleophile on the linker compound with a reactive group of an active agent or by coupling a nucleophile on an active agent with a reactive group on a linker compound, followed by contacting the trihydroxyphenyl-treated substrate with a solution of the active agent-linker conjugate. The active agent adsorbs to/adheres to/couples to/associates with a linker compound through covalent bond formation, hydrogen bond formation, ionic bond formation, van der Waals interactions, or combinations of the foregoing. The linker compound can be any linker compound as previously described herein. Typically, the active agent is coupled to a linker compound by forming one or more covalent bonds with an end group of the linker compound. It is believed that when the linker couples to the active agent through a reactive group including, but not limited to carboxyls, carboxylates, amides, acyl halides, aldehydes, and esters, the linker is coupled to the active agent through the reactive group on the linker and a nucleophilic group on the active agent. It is further believed that when the reactive group of the linker is a nucleophile such as hydroxyl, alkoxide, amine, nitrite, thiol, and thiolate, the linker can couple to a reactive group of an active agent, including but not limited to heparin, chitosan, quaternary chitosan, etc., through the nucleophilic group on the linker compound.

The active agent-linker conjugate can be formed by combining in solution a linker compound and an active agent. In embodiments of the invention wherein the active agent is a liquid, the active agent can be the solvent (or medium) in which the active agent-linker conjugate is formed. In embodiments of the invention wherein a solution of an active agent is combined with a solution of a linker compounds, the solutions of the active agents and the linker compounds can be prepared in any solvent capable of acting as a carrier for the active agent and/or the linker compound. For example, most frequently water is used, but organic solvents including but not limited to, alcohols, diols, organosulfurs such as sulfolane, ethers, such as diethyl ether and tetrahydrofuran, alkanes, aromatics, halocarbons, such as chloroform and dichloromethane, and combinations of the foregoing can also be used.

In refinements of the aforementioned embodiment, the solutions of active agent and/or linker compound is at a pH in a range of about 5.5 to about 9.5, or about 8 to about 9, or about 8.5, or about 6 to about 8, or about 7.5. The solution of active agent and/or solution of linker compound may further include a buffer in order to maintain the pH within the foregoing ranges, including, but not limited to, N,N-bis(2-hydroxyethyl)glycine (Bicine), 3-{[tris(hydroxymethyl)methyl]amino}propanesulfonic acid (TAPS), tris(hydroxymethyl)methylamine (Tris), and N-tris(hydroxymethyl)methylglycine (Tricine). Of course, one or more of carbonate, phosphate and other known buffer systems for maintaining relatively higher pH values can also be used.

In alternative embodiments, the solutions of active agent and/or linker compound can be maintained at a lower pH. For example, acetate buffered solutions can be used, having a pH in a range of about 4 to about 5.5, for example, about 4.0 about 4.1, about 4.2, about 4.3, about 4.4, about 4.5, about 4.6, about 4.7, about 4.8, about 4.9, about 5, about 5.1, about 5.2, about 5.3, about 5.4, and/or about 5.5, when coupling the active agent to the linker compound to form the active agent-linker conjugate. Suitable active agents for coupling to linker compounds at lower pH include, but are not limited to, heparin and chitosan. The solutions of active agent and/or linker compound may further include a buffer in order to maintain the pH within the foregoing ranges as is well known in the art. Suitable buffers for maintaining such a pH include one or more of acetate, citrate, lactate, phosphate and other known buffer systems can also be used.

The concentrations of the active agent and linker compound in solution can be any concentration. In some embodiments, the active agent can be directly added to a solution of the linker compound, without first forming an active agent solution. In alternative embodiments, the active agent can be provided to a solution of the linker compound in an active agent solution. The concentrations are typically chosen such that the active agent and/or linker compound are fully soluble in a chosen solvent, without forming saturated solutions. Exemplary active agent and/or linker compound concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml and/or about 3 mg/ml. The ratio of active agent to linker compound can be in a range of about 1:8 to about 8:1, about 1:7 to about 7:1, about 1:6 to about 6:1, about 1:5 to about 5:1, about 1:4 to about 4:1, about 1:3 to about 3:1, and/or about 1:2 to about 2:1, for example about 1:1.

The active agent-linker conjugate can be coupled to the trihydroxyphenyl-treated substrate by contacting the trihydroxyphenyl-treated substrate with a solution of active agent-linker conjugate. The trihydroxyphenyl-treated substrate can be completely immersed in the solution of the active agent-linker conjugate, for example, by dip coating. Alternatively, a solution of the active agent-linker conjugate can be sprayed or cast onto the substrate, for example, by spin casting or spraying a solution such as an aerosolized solution. For substrates having an interior lumen, such as tubing, the solution can be flowed into the lumen to coat the interior thereof.

The concentration of the active agent-linker conjugate in the active agent-linker conjugate solution can be any concentration. The concentration of the active agent-linker conjugate is typically chosen such that the active agent-linker conjugate is fully soluble in a chosen solvent, without forming a saturated solution. Exemplary active agent-linker conjugate concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml or about 3 mg/ml.

The trihydroxyphenyl-treated substrate can be contacted with and/or immersed in the solution of the active agent-linker conjugate for any duration suitable to couple the active agent-linker conjugate to the trihydroxyphenyl-treated substrate. It is believed that the active agent-linker conjugate can couple to the trihydroxyphenyl-treated substrate through either or both of the end group of the linker compound distal from the active agent and residual nucleophilic groups on the active agent. In embodiments of the invention the duration of contact can be any duration of time suitable for forming a covalent bond between one or more of the linker or active agent with the trihydroxyphenyl group of the trihydroxyphenyl-treated substrate. The rate of the coupling of the active agent-linker conjugate to the trihydroxyphenyl-treated substrate can depend, in part, on the concentration of the active agent-linker conjugate solution thereof, the substrate surface to solution volume ratio, the ionic strength of the solution, the pH of the solution, and the temperature. The duration of contact of the trihydroxyphenyl-treated substrate with the solution of active agent-linker conjugate can be varied for any suitable time period for coupling the active agent-linker conjugate to the trihydroxyphenyl-treated substrate, for example, when using dip coating, from about 10 seconds to about 24 hours. When the duration of contact of the substrate with the solution of active agent-linker conjugate increases above 24 hours (and one of the foregoing exemplary concentrations of active agent-linker conjugate is used), little difference in the amount of active agent immobilized to the substrate surface is expected (relative to a 24 hour exposure time). Without intending to be bound by theory, while it is believed that the active agent-linker conjugate may continue to be immobilized on the substrate, it is expected that the amount of the active agent immobilized after 24 hours will have little effect on the activity (antibacterial, antimicrobial, etc.) of the resulting substrate having an active agent immobilized thereto.

Active Agent-trihydroxyphenyl Conjugates with Optional Linker

In embodiments of the invention, an active agent-trihydroxyphenyl conjugate is initially formed by coupling a nucleophile of the active agent with a reactive group on the trihydroxyphenyl group or by coupling a nucleophile of the trihydroxyphenyl group with a reactive group of the active agent, followed by contacting the substrate with a solution of the active agent-trihydroxyphenyl conjugate. The active agent-trihydroxyphenyl conjugate can be formed by combining in solution a compound including a trihydroxyphenyl group and an active agent. As described previously, the compound including a trihydroxyphenyl group includes trihydroxyphenyl-linker conjugates. Therefore, the active agent-trihydroxyphenyl conjugate encompasses active agents coupled to linker compounds that are further coupled to trihydroxyphenyl groups. Active agents coupled to linker compounds can be formed as described above for active agent-linker conjugates and compounds including trihydroxyphenyl groups coupled to linker compounds can be formed as described above for trihydroxyphenyl-linker conjugates. These can then be further reacted with a compound including trihydroxyphenyl group or active agent, respectively, to form active agent-trihydroxyphenyl conjugates. Generic trihydroxyphenyl-active agent conjugates can be represented by formulae (Va-c) and (VIa-c):

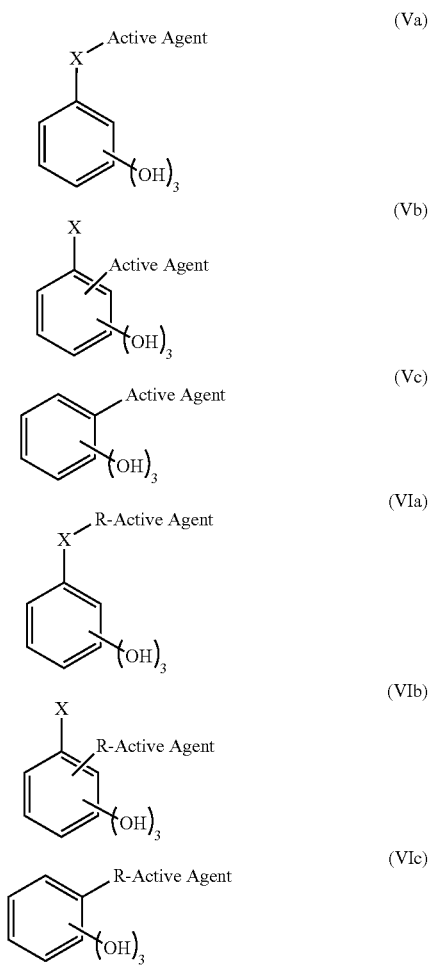

wherein X can be halogen, amine, thiol, aldehyde, carboxylic acid, carboxylate, acyl halide, ester, acrylate, vinyl, C1 to C10 branched or linear alkyl amine, C1 to C10 branched or linear alkyl thiol, C1 to C10 branched or linear alkyl aldehyde, C1 to C10 branched or linear alkyl carboxylic acid, C1 to C10 branched or linear alkyl carboxylate, C1 to C10 branched or linear alkyl acyl halide, C1 to C10 branched or linear alkyl ester, or C1 to C10 branched or linear alkyl acrylate, and R is a linker compound. With respect to the length of the carbon chains of the listed substituents, the chain length is typically C1 to C5 when aqueous solutions are used (as long as solubility is achieved in the selected aqueous system); when organic solvents are used, the chain length can be C1 to C10. In accordance with compounds (Va-c) and (VIa-c), the three hydroxyl groups can be provided on any three of $C_2$, $C_3$, $C_4$, $C_5$, and $C_6$. For example, when the compound including a trihydroxyphenyl group is a carboxylic acid such as gallic acid (and thus X is carboxyl), the active agent-trihydroxyphenyl conjugate can be of formula (Va), (Vb), (VIa), or (VIb):

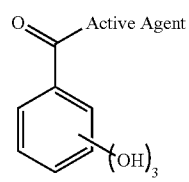

(Va)

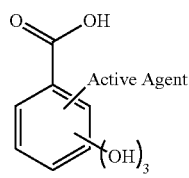

(Vb)

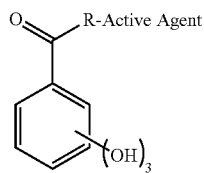

(VIa)

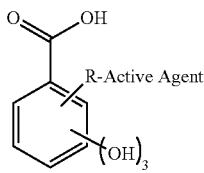

(VIb)

wherein R is the linker compound and Active Agent denotes an active agent. Further, when the compound including a trihydroxyphenyl group is gallic acid, consistent with the active agent-trihydroxyphenyl conjugates according to (Va), (Vb), (VIa), and (VIb), the three hydroxyl groups are provided on $C_3$, $C_4$, and $C_5$, and the linker is provided on the carboxyl group (IVa) or one of $C_2$ or $C_6$ (IVb). When the compound including a trihydroxyphenyl group is pyrogallol, the active agent-trihydroxyphenyl conjugate can be of formula (Vc) or (VIc):

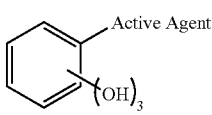

(Vc)

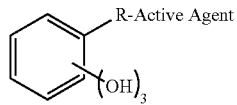

(VIc)

wherein R is the linker compound and the three hydroxyl groups can be provided on any consecutive three of $C_2$, $C_3$, $C_4$, $C_5$, and $C_6$.

In embodiments of the invention wherein the active agent is provided as a neat liquid, the active agent can be the solvent in which the active agent-trihydroxyphenyl conjugate is formed. In embodiments of the invention wherein a solution of an active agent is combined with a solution of a compound including a trihydroxyphenyl group, the solution of the active agent and/or the compound including a trihydroxyphenyl group can be prepared in any solvent capable of acting as a carrier for the active agent and/or the compound including a trihydroxyphenyl group. For example, most frequently water is used, but organic solvents including but not limited to, alcohols, diols organosulfurs such as sulfolane, ethers, such as diethyl ether and tetrahydrofuran, alkanes, aromatics, halocarbons, such as chloroform and dichloromethane, and combinations of the foregoing can also be used.

In refinements of the aforementioned embodiment, the solution of active agent and/or solution of compound including a trihydroxyphenyl group is at a pH in a range of about 7.5 to about 9.5, or about 8 to about 9, or about 8.5. The solution of active agent and/or solution of compound including a trihydroxyphenyl group may further include a buffer in order to maintain the pH within the foregoing ranges, including, but not limited to, N,N-bis(2-hydroxyethyl)glycine (Bicine), 3-{[tris(hydroxymethyl)methyl]amino}propanesulfonic acid (TAPS), tris(hydroxymethyl)methylamine (Tris), and N-tris(hydroxymethyl)methylglycine (Tricine). Of course, one or more of citrate, carbonate, lactate, phosphate and other known buffer systems can also be used. In alternative embodiments, solution of active agent and/or solution of compound including a trihydroxyphenyl group can have a lower pH. For example, acetate buffered solutions can be used for deposition of active agents at a pH in a range of about 4 to about 5.5, for example, about 4.0, about 4.1, about 4.2, about 4.3, about 4.4, about 4.5, about 4.6, about 4.7, about 4.8, about 4.9, about 5, about 5.1, about 5.2, about 5.3, about 5.4, and/or about 5.5. Suitable active agents for coupling to a compound including a trihydroxyphenyl group in solution at lower pH include, but are not limited to, heparin.

The concentrations of the active agent and compound including a trihydroxyphenyl group in solution can generally be any concentration. In some embodiments, the active agent can be directly added to a solution of the compound including a trihydroxyphenyl group, without first forming an active agent solution. In alternative embodiments, the active agent can be provided to a solution of the compound including a trihydroxyphenyl group in an active agent solution. The concentrations are typically chosen such that the active agent and/or compound including a trihydroxyphenyl group are fully soluble in a chosen solvent, without forming saturated solutions. Exemplary active agent and/or compound including a trihydroxyphenyl group concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml and/or about 3 mg/ml. The ratio of active agent to compound including a trihydroxyphenyl group can vary depending on if the active agent is a small molecule or a polymer, as well as if the compound including a trihydroxyphenyl group is a small molecule or a polymer. For example, when the active agent is a polymer and the compound including a trihydroxyphenyl group is a small molecule, one active agent could couple to thousands of compounds including a trihydroxyphenyl group. Alternatively, when the active agent is a small molecule and the compound including a trihydroxyphenyl group is a polymer, one compound including a trihydroxyphenyl group could couple to thousands of active agents. Suitable ratios of active agents to compounds including a trihydroxyphenyl can, therefore, be in a range of about 1:5,000 to about 5,000:1, including all intermediate ranges, such as about 1:5 to about 5:1, about 1:4 to about 4:1, about 1:3 to about 3:1, and/or about 1:2 to about 2:1, for example about 1:1.

Coupling of the Active Agent-trihydroxyphenyl Conjugate and the Substrate

The active agent-trihydroxyphenyl conjugate can be coupled to the substrate by contacting the substrate with a solution of active agent-trihydroxyphenyl conjugate. The substrate can be completely immersed in the solution of the active agent-trihydroxyphenyl conjugate, for example, by dip coating. Alternatively, a solution of the active agent-trihydroxyphenyl conjugate can be sprayed or cast onto the substrate, for example, by spin casting or spraying using a solution such as an aerosolized solution. For substrates having an interior lumen, such as tubing, the solution can be flowed into the lumen to coat the interior thereof.

The concentration of the active agent-trihydroxyphenyl conjugate in the active agent-trihydroxyphenyl conjugate solution can be any concentration. The concentration of the active agent-trihydroxyphenyl conjugate is typically chosen such that the active agent-trihydroxyphenyl conjugate is fully soluble in a chosen solvent, without forming a saturated solution. Exemplary active agent-trihydroxyphenyl conjugate concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml or about 3 mg/ml.

The substrate can be contacted with and/or immersed in the solution of the active agent-trihydroxyphenyl conjugate for any duration of time suitable to couple the trihydroxyphenyl group of the active agent-trihydroxyphenyl conjugate to the substrate surface. In embodiments of the invention, the substrate can be contacted with and/or immersed in the solution of the active agent-trihydroxyphenyl conjugate for any duration of time suitable to form covalent bonds between the trihydroxyphenyl group and a reactive moiety (when present) on the substrate surface. In alternative embodiments, the substrate can be contacted with and/or immersed in the solution of the active agent-trihydroxyphenyl conjugate for any duration of time suitable to chelate the trihydroxyphenyl group of the active agent-trihydroxyphenyl conjugate to a metal ion of a metallic substrate surface. The rate of the coupling of the active agent-trihydroxyphenyl conjugate and the substrate can depend, in part, on the concentration of the active agent-trihydroxyphenyl conjugate in the active agent-trihydroxyphenyl conjugate solution, the substrate surface to solution volume ratio, the ionic strength of the solution, the pH of the solution, and the temperature. The duration of contact of the substrate with the solution of active agent-trihydroxyphenyl conjugate can be varied for any suitable time period for coupling the trihydroxyphenyl group with the substrate surface, for example, when using dip coating, from about 10 seconds to about 24 hours. When the duration of contact of the substrate with the solution of active agent-trihydroxyphenyl conjugate increases above 24 hours (and one of the foregoing exemplary concentrations of active agent-trihydroxyphenyl conjugate is used), little difference in the amount of active agent immobilized to the substrate surface is expected (relative to a 24 hour exposure time). Without intending to be bound by theory, while it is believed that the active agent-trihydroxyphenyl conjugate may continue to be immobilized on the substrate, it is expected that the amount of the active agent immobilized after 24 hours will have little effect on the activity (antibacterial, antimicrobial, etc.) of the resulting substrate having an active agent immobilized thereto.

The methods, substrates, and medical devices in accordance with the invention can be better understood in light of the following examples, which are merely intended to illustrate the methods, substrates, and medical devices and are not meant to limit the scope thereof in any way.

EXAMPLES

Example 1

Immobilization of Polyethylenimine to Stainless Steel Substrate by Coupling with Pyrogallol A model antimicrobial active agent, polyethylenimine (denoted PEI in Table 1), was immobilized onto a stainless steel (SS) substrate. The substrate was put into a container, rinsed with isopropanol for about 5 min and then rinsed well with filtered, distilled water. The substrate was then exposed to a pyrogallol solution having a pyrogallol concentration of 2.5 mg/mL in 0.1M bicine (pH of 8) by adding 3 mL of solution to the substrate container to form a pyrogallol-treated substrate. The pyrogallol-treated substrate was put on a shaker at room temperature for about 24 hours. The substrate was then rinsed with filtered, distilled water. Based on the silver nitrate test, data not shown (see also Example 16), we concluded that any material remaining on the pyrogallol-treated substrate after agitation and rinsing was attributable to pyrogallol coupled to the substrate. 3 mL of a 2.5% PEI in 0.1M bicine (pH of 8) solution was added to the substrate, and the substrate was put on a shaker for about 24 hours. The substrate was then rinsed with filtered, distilled water several times. As a result of the preceding agitation and rinsing, and in view of the acid orange testing discussed below, we concluded that any material remaining on the substrate (relative to a negative control) corresponds to PEI coupled to the pyrogallol treated substrate.

The substrate was then tested to corroborate that the PEI was immobilized on the surfaces of the substrates. 2 mL of 500 µmol/L acid orange solution (pH or 3) was added to the substrate container the substrate was put on a shaker for about 24 hours. The free dissolved acid orange was then removed with an aqueous rinse (pH of 3). Following this rinse, 2 mL of a basic aqueous solution (pH of 12) was added to the container to solubilize the surface bound acid orange dye from the substrate. A 200 µL aliquot of the basic solution was pipetted from the container and transferred to a 96 well plate. The absorbance was read on a UV/VIS spectrophotometer at 492 nm. The absorbance value was corrected by subtracting the absorbance corresponding to a similarly treated container which contained no substrate. The corrected absorbance was found to be 0.396. This value corroborates our conclusion that the immobilization of PEI on a stainless steel substrate using pyrogallol is accomplished under the conditions described herein. An absorbance value above 0.1 is considered to demonstrate successful immobilization of the active agent to the substrate. The acid orange test is specific for amine and imine functionality and the successful formation of a colorimetric solution using this agent is indicative of the presence of amine/imine functionality and therefore corroborates that PEI is coupled to the trihydroxyphenyl-treated substrate.

Thus, Example 1 illustrates the immobilization of polyethylenimine onto stainless steel according to the invention using a compound including a trihydroxyphenyl group, pyrogallol, according to the invention.

Example 2

Immobilization of Polyethylenimine to Activated Stainless Steel Substrate by Coupling with Phloroglucinol A model antimicrobial active agent, polyethylenimine (denoted PEI in Table 1), was immobilized onto a stainless steel (SS) substrate. The substrate was put into a container, rinsed with isopropanol for about 5 min and then rinsed well with filtered, distilled water. The substrate was activated with an air plasma for 2 minutes. The substrate was then exposed to a phloroglucinol solution having a phloroglucinol concentration of 2.5 mg/mL in 0.1M bicine (pH of 8) by adding 3 mL of solution to the substrate container to form a phloroglucinol-treated substrate. The phloroglucinol-treated substrate was put on a shaker at room temperature for about 24 hours. The substrate was then rinsed with filtered, distilled water. We concluded that any material remaining on the substrate after agitation and rinsing was attributable to phloroglucinol coupled to the substrate. 3 mL of a 2.5% PEI in 0.1M bicine (pH of 8) solution was added to the substrate, and the substrate was put on a shaker for about 24 hours. The substrate was then rinsed with filtered, distilled water several times. As a result of the preceding rinses, we concluded that any material remaining on the substrate (relative to a negative control) corresponds to PEI coupled to the phloroglucinol-treated substrate.

The substrate was then tested to corroborate that the PEI was immobilized on the surfaces of the substrate. 2 mL of 500 µmol/L acid orange solution (pH or 3) was added to the substrate container the substrate was put on a shaker for about 24 hours. The free dissolved acid orange was then removed with an aqueous rinse (pH of 3). Following this rinse, 2 mL of a basic aqueous solution (pH of 12) was added to the container to solubilize the surface bound acid orange dye from the substrate. A 200 µL aliquot of the basic solution was pipetted from the container and transferred to a 96 well plate. The absorbance was read on a UV/VIS spectrophotometer at 492 nm. The absorbance value were corrected for controls by subtracting the absorbance corresponding to a similarly treated container which contained no substrate. The corrected absorbance was found to be 0.111. This value corroborates our conclusion that PEI is immobilized to activated stainless steel using phloroglucinol under the conditions described herein.

Thus Example 2 illustrates the immobilization of polyethylenimine onto activated stainless steel according to the invention using a compound including a trihydroxyphenyl group, phloroglucinol, according to the invention.

Example 3

Immobilization of Polyethylenimine to Activated Nickel Substrate by Coupling with Various Compounds Including a Trihydroxyphenyl Group A model antimicrobial active agent, polyethylenimine (denoted PEI in Table 1), was immobilized onto nickel (Ni) substrates. The substrates were put into separate containers, rinsed with isopropanol for about 5 min and then rinsed well with filtered, distilled water. The substrates were activated with an air plasma for 2 minutes. The substrates was then exposed to one of a gallic acid, pyrogallol, benzenetriol, or phloroglucinol solution having a concentration of 2.5 mg/mL compound including a trihydroxyphenyl group in 0.1M bicine (pH of 8) by adding 3 mL of solution to each substrate container, so as to form a trihydroxyphenyl treated substrate. The trihydroxyphenyl-treated substrates were put on a shaker at room temperature for about 24 hours. The substrates were then rinsed with filtered, distilled water. Based on the silver nitrate test, data not shown (see also Example 16), we concluded that any material remaining on the pyrogallol-treated substrate after agitation and rinsing was attributable to pyrogallol coupled to the substrate. 3 mL of a 2.5% PEI in 0.1M bicine (pH of 8) solution was added to the trihydroxyphenyl-treated substrates, and the substrates were put on a shaker for about 24 hours. The substrates were then rinsed with filtered, distilled water several times. As a result of the preceding rinses, and in view of the acid orange testing discussed below, we concluded that any material remaining on the substrates (relative to a negative control) corresponds to PEI coupled to the trihydroxyphenyl-treated substrate.

The substrates were then tested to corroborate that the PEI was immobilized on the surfaces of the substrate. 2 mL of 500 µmol/L acid orange solution (pH or 3) was added to each substrate container the substrates were put on a shaker for about 24 hours. The free dissolved acid orange was then removed with an aqueous rinse (pH of 3). Following this rinse, 2 mL of a basic aqueous solution (pH of 12) was added to the containers to solubilize the surface bound acid orange dye from the substrates. A 200 µL aliquot of the basic solution was pipetted from each container and transferred to a 96 well plate. The absorbance was read on a UV/VIS spectrophotometer at 492 nm. The absorbance values were corrected for controls by subtracting the absorbance corresponding to a similarly treated container which contained no substrate. The absorbance data is found in Table 1. These values corroborates our conclusion that PEI is immobilized to activated nickel using various compounds including a trihydroxyphenyl group under the conditions described herein.

TABLE 1

| Absorbances-corrected | Ni |
|---|---|
| Plasma/Gallic acid/PEI | 0.092 |
| Plasma/Pyrogallol/PEI | 0.126 |
| Plasma/Benzenetriol/PEI | 0.165 |
| Plasma/Phloroglucinol/PEI | 0.012 |

Thus Example 3 illustrates the immobilization of polyethylenimine onto activated nickel according to the invention using various compounds including a trihydroxyphenyl group according to the invention.

Example 4

Immobilization of Polyethylenimine to Titanium Substrates by Coupling with Various Compounds Including a Trihydroxyphenyl Group A model antimicrobial active agent, polyethylenimine (denoted PEI in Table 1), was immobilized onto titanium (Ti) substrates. All substrates were put into separate containers, rinsed with isopropanol for about 5 min and then rinsed well with filtered, distilled water. The substrates were then exposed to one of a gallic acid, pyrogallol, benzenetriol, or phloroglucinol solution having a concentration of 2.5 mg/mL compound including a trihydroxyphenyl group in 0.1M bicine (pH of 8) by adding 3 mL of solution to each substrate container, so as to form a trihydroxyphenyl treated substrate. The trihydroxyphenyl treated substrates were put on a shaker at room temperature for about 24 hours. Each the substrates was then rinsed with filtered, distilled water. Based on the silver nitrate test, data not shown (see also Example 16), we concluded that any material remaining on the pyrogallol-treated substrate after agitation and rinsing was attributable to pyrogallol coupled to the substrate. 3 mL of a 2.5% PEI in 0.1M bicine (pH of 8) solution was added to each substrate, and the trihydroxyphenyl substrates were put on a shaker for about 24 hours. The substrates were then rinsed with filtered, distilled water several times. As a result of the preceding agitation and rinsing, and in view of the acid orange testing discussed below, we concluded that any material remaining on the substrates (relative to a negative control) corresponds to PEI coupled to the trihydroxyphenyl treated substrates.

The substrates were then tested to corroborate that the PEI was immobilized on the surfaces of the substrates. 2 mL of 500 μmol/L acid orange solution (pH or 3) was added to each substrate container the substrates were put on a shaker for about 24 hours. The free dissolved acid orange was then removed with an aqueous rinse (pH of 3). Following this rinse, 2 mL of a basic aqueous solution (pH of 12) was added to each container to solubilize the surface bound acid orange dye from the substrate. A 200 μL aliquot of the basic solution was pipetted from each container and transferred to a 96 well plate. The absorbance was read on a UV/VIS spectrophotometer at 492 nm. The absorbance values were corrected for controls by subtracting the absorbance corresponding to a similarly treated container which contained no substrate. The absorbance data is shown in Table 2. The obtained values corroborate our conclusion that PEI is immobilized to titanium substrates using various compounds including a trihydroxyphenyl group under the conditions described herein.

In this example, the conditions for coupling the compound including a trihydroxyphenyl group to the substrate were the same for each compound including a trihydroxyphenyl group that was tested. However, we expect that the optimization of the pH of the buffer for each compound including a trihydroxyphenyl group and/or the concentration of the solutions of compounds including a trihydroxy group and/or active agents would lead to further enhanced results, particularly for compounds including a trihydroxyphenyl group where relatively small absorbance values were observed and/or no coating was apparently formed (e.g., benzenetriol).

TABLE 2

| Absorbances-corrected | Ti |
|---|---|
| Gallic acid/PEI | 0.825 |
| Pyrogallol/PEI | 0.035 |
| Benzenetriol/PEI | 0 |
| Phloroglucinol/PEI | 0.627 |

Thus Example 4 illustrates the immobilization of polyethylenimine onto titanium substrates according to the invention using various compounds including a trihydroxyphenyl group according to the invention.

Example 5

Immobilization of Polyethylenimine to Silica Substrates by Coupling with Various Compounds Including a Trihydroxyphenyl Group A model antimicrobial active agent, polyethylenimine (PEI), was immobilized onto silicon dioxide glass microscope slides of about 1.5 cm×1.5 cm. All substrates were put into individual containers, rinsed with isopropanol for about 5 min and then rinsed well with filtered, distilled water. The substrates were then exposed to one of a gallic acid, pyrogallol, benzenetriol, or phloroglucinol solution having a concentration of 2.5 mg/mL compound including a trihydroxyphenyl group in 0.1M bicine (pH of 8) by adding 3 mL of solution to each container so as to form trihydroxyphenyl-treated substrates. The trihydroxyphenyl treated substrates were put on a shaker at room temperature for about 24 hours. Each of the substrate containers were then rinsed with filtered, distilled water several times. Based on the silver nitrate test, data not shown (see also Example 16), we concluded that any material remaining on the pyrogallol-treated substrate after agitation and rinsing was attributable to pyrogallol coupled to the substrate. 3 mL of a 2.5% PEI in 0.1M bicine (pH of 8) solution was added to each container and the substrates were put on a shaker for about 24 hours. The substrates were then rinsed with filtered, distilled water several times. As a result of the preceding agitation and rinsing, and in view of the acid orange testing discussed below, we concluded that any material remaining on the substrate (relative to a negative control) corresponds to PEI coupled to the trihydroxyphenyl treated substrates.

The substrates were then tested to corroborate that the PEI was immobilized on the surfaces of the substrates. 2 mL of 500 μmol/L acid orange solution (pH or 3) was added to each substrate and the substrates were put on a shaker for about 24 hours. The free dissolved acid orange was then removed with an aqueous rinse (pH of 3). Following this rinse, 2 mL of a basic aqueous solution (pH of 12) was added to each substrate to solubilize the surface bound acid orange dye from the substrate. A 200 μL aliquot of the basic solution was pipetted from each container and transferred to a 96 well plate. The absorbance was read on a UV/VIS spectrophotometer at 492 nm. The absorbance values were corrected for controls by subtracting the absorbance corresponding to a similarly treated container which contained no substrate. The absorbance data is shown in Table 3. The obtained values (other than the value for phloroglucinol, discussed in further detail below) corroborate our conclusion that PEI is immobilized to silica substrates using various compounds including a trihydroxyphenyl group under the conditions described herein.

In this example, the conditions for coupling the compound including a trihydroxyphenyl group to the substrate were the same for each compound including a trihydroxyphenyl group that was tested. However, the inventors expect that the optimization of the pH of the buffer for each compound including a trihydroxyphenyl group and/or concentration of the solutions of compounds including a trihydroxy group and/or active agents would lead to further enhanced results, particularly for compounds including a trihydroxyphenyl group where relatively small absorbance values were observed and/or no coating was apparently formed (e.g., phloroglucinol).

TABLE 3

| Absorbances-corrected | Glass |
|---|---|
| Gallic acid/PEI | 0.665 |
| Pyrogallol/PEI | 0.467 |
| Benzenetriol/PEI | 0.041 |
| Phloroglucinol/PEI | 0 |

Thus Example 5 illustrates the immobilization of polyethylenimine onto silica substrates of the invention through coupling with various compounds including a trihydroxyphenyl group of the invention.

Example 6

Immobilization of Polyethylenimine to Polymer Substrates by Coupling with Various Compounds Including a Trihydroxyphenyl Group A model antimicrobial active agent, polyethylenimine (PEI), was immobilized onto one of a polyisoprene (PI) (1.5 cm×1.5 cm squares), polycarbonate (PC) (received and used as small circles), or polysulfone (PS) (received and used as small squares) substrate. All substrates were put into individual containers, rinsed with isopropanol for about 5 min and then rinsed with filtered, distilled water. The substrates were then exposed to one of a gallic acid, pyrogallol, benzenetriol, or phloroglucinol solution having a concentration of 2.5 mg/mL compound including a trihydroxyphenyl group in 0.1M bicine (pH of 8) by adding 3 mL of solution to each substrate container so as to form trihydroxyphenyl treated substrates. The containers were put on a shaker at room temperature for about 24 hours. Each of the substrates were then rinsed with filtered, distilled water. Based on the silver nitrate test, data not shown (see also Example 16), we concluded that any material remaining on the pyrogallol-treated substrate after agitation and rinsing was attributable to pyrogallol coupled to the substrate. 3 mL of a 2.5% PEI in 0.1M bicine (pH of 8) solution was added to each substrate, and the substrates were put on a shaker for about 24 hours. The substrates were then rinsed with filtered, distilled water several times. As a result of the preceding agitation and rinsing, and in view of the acid orange testing discussed below, we concluded that any material remaining on the substrate (relative to a negative control) corresponds to PEI coupled to the pyrogallol treated substrate.

The substrates were then tested to corroborate that the PEI was immobilized on the surfaces of the substrates. 2 mL of 500 μmol/L acid orange solution (pH or 3) was added to each substrate and the substrates were put on a shaker for about 24 hours. The free dissolved acid orange was then removed with an aqueous rinse (pH of 3). Following this rinse, 2 mL of a basic aqueous solution (pH of 12) was added to each substrate to solubilize the surface bound acid orange dye from the substrate. A 200 μL aliquot of the basic solution was pipetted from each container and transferred to a 96 well plate. The absorbance was read on a UV/VIS spectrophotometer at 492 nm. The absorbance values were corrected for controls by subtracting the absorbance corresponding to a similarly treated container which contained no substrate. The absorbance data is shown in Table 4. The obtained values corroborate our conclusion that PEI is immobilized to various polymer substrates using various compounds including a trihydroxyphenyl group under the conditions described herein.

In this example, the conditions for coupling the compound including a trihydroxyphenyl group to the substrate were the same for each compound including a trihydroxyphenyl group that was tested. However, we expect that the optimization of the pH of the buffer for each compound including a trihydroxyphenyl group and/or concentrations of the solutions of compounds including a trihydroxy group and/or active agents would lead to further enhanced results, particularly for compounds including a trihydroxyphenyl group where relatively small absorbance values were observed and/or no coating was apparently formed (e.g., phloroglucinol).

TABLE 4

| Absorbances-corrected | PC | PS | PI |
|---|---|---|---|
| Gallic acid/PEI | 0.108 | 0.557 | 0.762 |
| Pyrogallol/PEI | 0.332 | 0.028 | 1.077 |
| Benzenetriol/PEI | 0.066 | 0.074 | 0 |
| Phloroglucinol/PEI | 0.006 | 0 | 0 |

Thus Example 6 illustrates the immobilization of polyethylenimine onto various polymer substrates according to the invention though coupling with various compounds including a trihydroxyphenyl group of the invention.

Example 7

Impact of Activation on the Coupling of Polyethylenimine to Various Substrates with Compounds Including a Trihydroxyphenyl Group A model antimicrobial active agent, polyethylenimine (PEI), was immobilized onto one of a titanium (Ti), silicon dioxide glass microscope slides of about 1.5 cm×1.5 cm (glass), polyisoprene (PI) (1.5 cm×1.5 cm squares), polycarbonate (PC) (received and used as small circles), or polysulfone (PS) (received and used as small squares) substrate. In conducting this experiment, the substrates were used as-is (denoted "No Act" in Table 4), or were activated with either an air plasma for 2 minutes (denoted as "Plasma") or with an $HCl/H_2O_2$ solution by immersing the substrate in a solution of $H_2O_2$:HCl (1:1 by volume) for 5 min (denoted "Acid") prior to treatment with a compound including a trihydroxyphenyl group. The titanium substrates were not activated with the peroxy-hydrochloric acid solution. The substrates were then exposed to one of a gallic acid, pyrogallol, benzenetriol, or phloroglucinol solution having a concentration of 2.5 mg/mL compound including a trihydroxyphenyl group in 0.1M bicine (pH of 8) by adding 3 mL of solution to each substrate container so as to form trihydroxyphenyl-treated substrates. The trihydroxyphenyl-treated substrates were put on a shaker at room temperature for about 24 hours. Each of the trihydroxyphenyl-treated substrates were then rinsed with filtered, distilled water. Based on the silver nitrate test, data not shown (see also Example 16), we concluded that any material remaining on the pyrogallol-treated substrate after agitation and rinsing was attributable to pyrogallol coupled to the substrate. 3 mL of a 2.5% PEI in 0.1M bicine (pH of 8) solution was added to each substrate container and the substrates were put on a shaker for about 24 hours. The substrates were then rinsed with filtered, distilled water several times. As a result of the preceding agitation and rinsing, and in view of the acid orange testing discussed below, we concluded that any material remaining on the substrates (relative to a negative control) corresponds to PEI coupled to the trihydroxyphenyl treated substrates.

The substrates were then tested to corroborate that the PEI was immobilized on the surfaces of the substrates. 2 mL of 500 μmol/L acid orange solution (pH or 3) was added to each substrate and the substrates were put on a shaker for about 24 hours. The free dissolved acid orange was then removed with an aqueous rinse (pH of 3). Following this rinse, 2 mL of a basic aqueous solution (pH of 12) was added to each substrate to solubilize the surface bound acid orange dye from the substrate. A 200 μL aliquot of the basic solution was pipetted from each container and put into a 96 well plate. The absorbance was read on a UV/VIS spectrophotometer at 492 nm. The absorbance values were corrected for controls by subtracting the absorbance corresponding to a similarly treated container which contained no substrate. The impact of the activation method on the coupling of the PEI to the substrates by the compounds including a trihydroxyphenyl group is shown in Table 5 by relative absorbance. The absorbance values corroborate our conclusion that PEI is immobilized to various substrates using various compounds including a trihydroxyphenyl group under the conditions described herein.

In this example, the conditions for coupling the compound including a trihydroxyphenyl group to the substrate were the same for each compound including a trihydroxyphenyl group that was tested, the conditions for activating the substrates were the same for each substrate, as were the concentrations of the solutions of the compounds including a trihydroxy group and/or active agents. However, we expect that the optimization of the pH of the buffer for each compound including a trihydroxyphenyl group, optimization of the exposure times of the substrate to the activator (e.g., air plasma, HCl/$H_2O_2$ solution), and/or the concentrations of the solutions of the compounds including a trihydroxy group and/or active agents would lead to further enhanced results, particularly for compounds including a trihydroxyphenyl group where relatively small absorbance values were observed and/or no coating was apparently formed.

TABLE 5

| Absorbances-corrected | glass | PC | PS | PI | Ti |
|---|---|---|---|---|---|
| No Act/Gallic acid/PEI | 0.665 | 0.108 | 0.557 | 0.762 | 0.825 |
| Plasma/Gallic acid/PEI | 0.346 | 0.031 | 0 | 0.65 | 0.778 |
| Acid/Gallic acid/PEI | 0.32 | 0.731 | 0.022 | 0.987 | — |
| No Act/Pyrogallol/PEI | 0.467 | 0.332 | 0.028 | 1.077 | 0.035 |

TABLE 5-continued

| Absorbances-corrected | glass | PC | PS | PI | Ti |
|---|---|---|---|---|---|
| Plasma/Pyrogallol/PEI | 1.029 | 0 | 0 | 0.479 | 0.002 |
| Acid/Pyrogallol/PEI | 0.886 | 0.011 | 0.001 | 0.728 | — |
| No Act/Benzenetriol/PEI | 0.041 | 0.066 | 0.074 | 0 | 0 |
| Plasma/Benzenetriol/PEI | 0.398 | 0 | 0 | 0 | 0.347 |
| Acid/Benzenetriol/PEI | 0 | 0.059 | 0 | 0 | — |
| No Act/Phloroglucinol/PEI | 0 | 0.006 | 0 | 0 | 0.627 |
| Plasma/Phloroglucinol/PEI | 0.137 | 0.019 | 0 | 0 | 0 |
| Acid/Phloroglucinol/PEI | 0 | 0.103 | 0.005 | 0.022 | — |

Thus Example 7 illustrates the impact that various forms of activation have on the immobilization of polyethylenimine onto various substrates according to the invention using various compounds including a trihydroxyphenyl group according to the invention.

Example 8

Immobilization of Polyethylene Glycol on a Stainless Steel Substrate

An antifouling active agent, polyethylene glycol (PEG), is immobilized onto the surface of a stainless steel substrate. A stainless steel substrate is immersed in a solution of 1.1 mg/mL gallic acid dissolved in 100 mM bicine (pH of 7.3). The stainless steel substrate is mildly agitated while immersed in the gallic acid solution at room temperature for about 24 hours. The substrate is removed from the solution and rinsed with filtered, distilled water. The resulting gallic acid treated substrate is immersed in a solution of $NH_2$-terminated PEG, SH-terminated PEG, and/or NHS-terminated PEG (1 mg/ml) dissolved in 300 mM acetate and 600 mM sodium chloride solution (pH 4.5). The gallic acid treated substrate is mildly agitated while immersed in the polyethylene glycol solution at room temperature for about 24 hours. The substrate is removed from the polyethylene glycol solution and rinsed with filtered, distilled water, resulting in a stainless steel substrate with PEG immobilized on the surface thereof. Immobilization of PEG can be confirmed using, for example, x-ray photoelectron spectroscopy (XPS) contact angle measurements, RAMAN spectrometry, or by time of flight secondary ion mass spectrometry (TOF-SIMS).

Thus, Example 8 illustrates how the immobilization of polyethylene glycol onto a stainless steel substrate can be achieved according to the invention.

Example 9

Immobilization of a Polyethylene Glycol-Gallic Acid Conjugate on a Stainless Steel Substrate An antifouling active agent, polyethylene glycol (PEG), is immobilized onto the surface of a stainless steel substrate. A polyethylene glycol-gallic acid conjugate solution is prepared by combining $NH_2$-terminated PEG, SH-terminated PEG, and/or NHS-terminated PEG (1 mg/ml) dissolved in 300 mM acetate and 600 mM sodium chloride solution (pH 4.5) with a solution of 1.1 mg/mL gallic acid dissolved in 100 mM bicine (pH of 7.3). A stainless steel substrate is immersed in the solution of polyethylene glycol-gallic acid conjugate. The substrate is mildly agitated while in the polyethylene glycol-gallic acid conjugate solution at room temperature for about 24 hours. The substrate is removed from the solution and rinsed with filtered, distilled water resulting in a stainless steel substrate with polyethylene glycol immobilized on the surface thereof. Immobilization of PEG can be confirmed using, for example, x-ray photoelectron spectroscopy (XPS) contact angle measurements, RAMAN spectrometry, or by time of flight secondary ion mass spectrometry (TOF-SIMS).

Thus, Example 9 illustrates how the immobilization of a polyethylene glycol-gallic acid conjugate onto a stainless steel substrate can be achieved according to the invention.

Example 10

Immobilization of Polyethylene Glycol on a Stainless Steel Substrate

An antifouling active agent, polyethylene glycol (PEG), is immobilized onto the surface of a stainless steel substrate. A gallic acid-linker conjugate solution is prepared by combining 1.1 mg/ml gallic acid dissolved in 100 mM bicine (pH of 7.3) and a 0.1M aqueous solution of 4-aminobutyric acid. A stainless steel substrate is immersed in the solution of gallic acid-linker conjugate. The stainless steel substrate is mildly agitated while immersed in the gallic acid-linker conjugate solution at room temperature for about 24 hours. The substrate is removed from the solution and rinsed with filtered, distilled water. The resulting gallic acid-treated substrate is immersed in a solution of $NH_2$-terminated PEG, SH-terminated PEG, and/or NHS-terminated PEG (1 mg/ml) dissolved in 300 mM acetate and 600 mM sodium chloride solution (pH 4.5). The gallic acid-treated substrate is mildly agitated while immersed in the polyethylene glycol solution at room temperature for about 24 hours. The substrate is removed from the polyethylene glycol solution and rinsed with filtered, distilled water, resulting in a stainless steel substrate with PEG immobilized on the surface thereof. Immobilization of PEG can be confirmed using, for example, x-ray photoelectron spectroscopy (XPS) contact angle measurements, RAMAN spectrometry, or by time of flight secondary ion mass spectrometry (TOF-SIMS).

Thus Example 10 illustrates how the immobilization of polyethylene glycol onto a stainless steel substrate can be achieved according to the invention.

Example 11

Immobilization of Polyethylene Glycol-Linker-Gallic Acid Conjugate on a Stainless Steel Substrate An antifouling active agent, polyethylene glycol (PEG), is immobilized onto the surface of a stainless steel substrate. A gallic acid-linker conjugate solution is prepared by combining 1.1 mg/ml gallic acid dissolved in 100 mM bicine (pH of 7.3) and a 0.1M aqueous solution of 4-aminobutyric acid. To the gallic acid-linker conjugate solution is added a solution of $NH_2$-terminated PEG, SH-terminated PEG, and/or NHS-terminated PEG (1 mg/ml) dissolved in 300 mM acetate and 600 mM sodium chloride solution (pH 4.5) to form a gallic acid-linker-PEG conjugate solution. A stainless steel substrate is immersed in the solution of gallic acid-linker-PEG conjugate. The stainless steel substrate is mildly agitated while immersed in the gallic acid-linker-PEG conjugate solution at room temperature for about 24 hours. The substrate is removed from the solution and rinsed with filtered, distilled water, resulting in a stainless steel substrate with PEG immobilized on the surface thereof. Immobilization of PEG can be confirmed using, for example, x-ray photoelectron spectroscopy (XPS) contact angle measurements, RAMAN spectrometry, or by time of flight secondary ion mass spectrometry (TOF-SIMS).

Thus Example 11 illustrates how the immobilization of polyethylene glycol onto a stainless steel substrate can be achieved according to the invention.

Example 12

Immobilization of Polyethylene Glycol on a Substrate Surface Through a Polymer Having a Pendant Trihydroxyphenyl Group An antifouling active agent, polyethylene glycol (PEG), is immobilized onto the surface of a stainless steel substrate. A monomer including a trihydroxyphenyl group is polymerized by radical polymerization. The chain transfer agent 2-mercaptopropoinic acid is added to the polymerization mixture to terminate polymerization, resulting in a polymer including at least one monomer having a pendant trihydroxyphenyl group. A 1 mg/mL solution of the resulting polymer in 0.1M bicine buffer at pH 7.5 is prepared. A stainless steel substrate is immersed in the solution of the polymer. The stainless steel substrate is mildly agitated while immersed in the polymer solution at room temperature for 24 hours. The substrate is removed from the solution and rinsed with filtered, distilled water. The resulting polymer treated substrate is immersed in a 1 mg/mL solution of $NH_2$-terminated PEG, SH-terminated PEG, and/or NHS-terminated PEG in 0.1 M Bicine buffer at pH 7.5. The polymer treated substrate is mildly agitated while immersed in the polyethylene glycol solution at room temperature for 24 hours. The substrate is removed from the polyethylene glycol solution and rinsed with filtered, distilled water, resulting in a stainless steel substrate with PEG immobilized on the surface thereof. Immobilization of PEG can be confirmed using, for example, x-ray photoelectron spectroscopy (XPS) contact angle measurements, RAMAN spectrometry, or by time of flight secondary ion mass spectrometry (TOF-SIMS).

Thus Example 12 illustrates how the immobilization of polyethylene glycol onto a stainless steel substrate can be achieved according to the invention.

Example 13

Immobilization of Polyethylene Glycol on a Substrate Surface Through a Polymer Having a Pendant Trihydroxyphenyl Group An antifouling active agent, polyethylene glycol (PEG), is immobilized onto the surface of a stainless steel substrate. A monomer including a trihydroxyphenyl group is polymerized by radical polymerization. The chain transfer agent 2-mercaptopropoinic acid is added to the polymerization mixture to terminate polymerization, resulting in a polymer including at least one monomer having a pendant trihydroxyphenyl group. A 1 mg/mL solution of the resulting polymer including at least one monomer having a pendant trihydroxyphenyl group in 0.1M Bicine buffer at pH 7.5 is prepared. A 1 mg/mL solution of $NH_2$-terminated PEG, SH-terminated PEG, and/or NHS-terminated PEG in 0.1M Bicine buffer at pH 7.5 is added to the polymer solution to form a gallic acid-linker-PEG conjugate solution. A stainless steel substrate is immersed in the solution of the gallic acid-linker-PEG conjugate. The stainless steel substrate is mildly agitated while immersed in the gallic acid-linker- PEG conjugate solution at room temperature for 24 hours. The substrate is removed from the solution and rinsed with filtered, distilled water, resulting in a stainless steel substrate with PEG immobilized on the surface thereof. Immobilization of PEG can be confirmed using, for example, x-ray photoelectron spectroscopy (XPS) contact angle measurements, RAMAN spectrometry, or by time of flight secondary ion mass spectrometry (TOF-SIMS).

Thus Example 13 illustrates how the immobilization of polyethylene glycol onto a stainless steel substrate can be achieved according to the invention.

Example 14

Silver Nitrate Test for Confirming the Immobilization of the Compound Including a Trihydroxyphenyl Group onto a Stainless Steel Substrate A variety of compounds including a trihydroxyphenyl group (THP) can be coupled to a substrate, and the immobilization of THP to the substrate can be confirmed using a silver nitrate test. A stainless steel substrate is immersed in a solution of one of a compound including a trihydroxyphenyl group, selected from gallic acid (2 mg/mL), pyrogallol (2 mg/mL), or 2,4,6-trihydroxybenzaldehyde (2 mg/mL) dissolved in 100 mM Bicine buffer (pH 7.5). The THP solution with the primed-substrate immersed therein is mildly agitated at room temperature for 24 hours. The substrate is removed from the THP solution and rinsed with filtered, distilled water. The resulting THP treated substrate is immersed in a solution of 50 mM silver nitrate for about 16 hours with mild agitation. The substrate is removed from the solution of silver nitrate and rinsed with filtered, distilled water. Any reducing groups on the compound including a trihydroxyphenyl group would be expected to reduce the silver nitrate if the THP was coupled to the substrate. The THP will reduce the silver ions to silver nanoparticles resulting in a brown stain to the substrate.

Thus, Example 14 illustrates how the immobilization of assorted THP groups onto a stainless steel substrate according to the invention can be confirmed.

Example 15

Immobilization of a Linker Compound onto a Trihydroxyphenyl Treated Substrate

An antifouling active agent, polyethylene glycol (PEG), is immobilized onto the surface of a stainless steel substrate. A gallic acid-linker conjugate solution is prepared by combining 1.1 mg/ml gallic acid dissolved in 100 mM bicine (pH of 7.3) and a 0.1M aqueous solution of 4-aminobutyric acid. A stainless steel substrate is immersed in the solution of gallic acid-linker conjugate. The stainless steel substrate is mildly agitated while immersed in the gallic acid-linker conjugate solution at room temperature for about 24 hours. The substrate is removed from the solution and rinsed with filtered, distilled water, resulting in a stainless steel substrate with a gallic acid-linker conjugate immobilized on the surface thereof. Immobilization of the gallic acid-linker conjugate can be confirmed using, for example, x-ray photoelectron spectroscopy (XPS) contact angle measurements, RAMAN spectrometry, or by time of flight secondary ion mass spectrometry (TOF-SIMS), or ATR-FTIR.

Thus, Example 15 illustrates how the immobilization of assorted linker compounds onto a stainless steel substrate according to the invention can be confirmed.

Example 16

Silver Nitrate Test for Determining the Immobilization of Gallic Acid onto Oxidized Polymeric Substrates Medically relevant polymeric materials, polyisoprene (PI), polycarbonate (PC) and polysulfone (PS) were modified with gallic acid. The surface of the substrates were oxidized by treating the surfaces with a solution of $H_2O_2$/HCl in a volume ratio of 1:1 for about 5 minutes, followed by rinsing with filtered distilled water (FDW) thereby introducing reactive moieties (hydroxyl groups) on the surface of the substrates. The oxidized substrates were immersed in a solution of 1.1 mg/mL gallic acid dissolved in 100 mM bicine (pH of 7.3). The substrates were mildly agitated while immersed in the gallic acid solution at room temperature for about 24 hours. The substrates were removed from the solution and rinsed with FDW. The resulting gallic acid-treated substrates were immersed in a 50 mM solution of silver nitrate. The substrates were mildly agitated while immersed in the silver nitrate solution at room temperature for about 60 hours. The polymeric substrates darkened in color denoting the deposition of silver metal onto the polymeric substrates. The metallization of the silver was due to the reducing capacity of the gallic acid layer on the substrate. If the gallic acid was not immobilized on the substrate the substrate would not have changed colors.

Thus, Example 16 illustrates how the immobilization of gallic acid onto polyisoprene, polycarbonate and polysulfone substrates was achieved according to the invention.

Example 17

Immobilization of Pyrogallol onto Oxidized Polymeric Substrates

Medically relevant polymeric materials, polyisoprene (PI), polycarbonate (PC) and polysulfone (PS) were modified with pyrogallol. The surface of the substrates were oxidized by treating the surface with a solution of $H_2O_2$/HCl in a volume ratio of 1:1 for about 5 minutes, followed by rinsing with filtered distilled water (FDW) thereby introducing reactive moieties (hydroxyl groups) on the surface of the substrates. The oxidized substrates were immersed in a solution of 1.4 mg/mL pyrogallol dissolved in 100 mM bicine (pH of 7.3). The substrates were mildly agitated while immersed in the pyrogallol solution at room temperature for about 24 hours. The substrates were removed from the solution and rinsed with FDW. The resulting pyrogallol-treated substrates were immersed in a 50 mM solution of silver nitrate. The substrates were mildly agitated while immersed in the silver nitrate solution at room temperature for about 60 hours. The polymeric substrates darkened in color denoting the deposition of silver metal onto the polymeric substrates. The metallization of the silver is due to the reducing capacity of the pyrogallol layer on the substrate.

Thus, Example 17 illustrates how the immobilization of pyrogallol onto polyisoprene, polycarbonate and polysulfone substrates was achieved according to the invention.

Example 18

Immobilization of Trihydroxybenzaldehyde onto Oxidized Polymeric Substrates

Medically relevant polymeric materials, polyisoprene (PI), polycarbonate (PC) and polysulfone (PS) were modified with trihydroxybenzaldehyde. The surface of the substrates were oxidized by treating the surfaces with a solution of $H_2O_2$/HCl in a volume ratio of 1:1 for about 5 minutes, followed by rinsing with filtered distilled water (FDW) thereby introducing reactive moieties (hydroxyl groups) on the surface of the substrates. The oxidized substrates were immersed in a solution of 1.1 mg/mL trihydroxybenzaldehyde dissolved in 100 mM bicine (pH of 7.3). The substrates were mildly agitated while immersed in the trihydroxybenzaldehyde solution at room temperature for about 24 hours. The substrates were removed from the solution and rinsed with FDW. The resulting trihydroxybenzaldehyde-treated substrates were immersed in a 50 mM solution of silver nitrate. The substrates were mildly agitated while immersed in the silver nitrate solution at room temperature for about 60 hours. The polymeric substrates darkened in color denoting the deposition of silver metal onto the polymeric substrates. The metallization of the silver is due to the reducing capacity of the trihydroxybenzaldehyde layer on the substrate.

Thus, Example 18 illustrates how the immobilization of trihydroxybenzaldehyde onto polyisoprene, polycarbonate and polysulfone substrates was achieved according to the invention.

Example 19

Immobilization of 1,2,4-Benzenetriol onto Oxidized Polymeric Substrates

Medically relevant polymeric materials, polyisoprene (PI), polycarbonate (PC) and polysulfone (PS) were modified with 1,2,4-benzenetriol. The surface of the substrates were oxidized by treating the surface with a solution of $H_2O_2$/HCl in a volume ratio of 1:1 for about 5 minutes, followed by rinsing with filtered distilled water (FDW) thereby introducing reactive moieties (hydroxyl groups) on the surface of the substrates. The oxidized substrates were immersed in a solution of 1.1 mg/mL 1,2,4-benzenetriol dissolved in 100 mM bicine (pH of 7.3). The substrates were mildly agitated while immersed in the 1,2,4-benzenetriol solution at room temperature for about 24 hours. The substrates were removed from the solution and rinsed with FDW. The resulting 1,2,4-benzenetriol-treated substrates were immersed in a 50 mM solution of silver nitrate. The substrates were mildly agitated while immersed in the silver nitrate solution at room temperature for about 60 hours. The polymeric substrates darkened in color denoting the deposition of silver metal onto the polymeric substrates. The metallization of the silver is due to the reducing capacity of the 1,2,4-benzenetriol layer on the substrate.

Thus, Example 19 illustrates how the immobilization of 1,2,4-benzenetriol onto polyisoprene, polycarbonate and polysulfone substrates was achieved according to the invention.

Example 20

Immobilization of Phloroglucinol onto Oxidized Polymeric Substrates

Medically relevant polymeric materials, polyisoprene (PI), polycarbonate (PC) and polysulfone (PS) were modified with phloroglucinol. The surface of the substrates were oxidized by treating the surface with a solution of $H_2O_2$/HCl in a volume ratio of 1:1 for about 5 minutes, followed by rinsing with filtered distilled water (FDW) thereby introducing reactive moieties (hydroxyl groups) on the surface of the substrates. The oxidized substrates were immersed in a solution of 1.3 mg/mL phloroglucinol dissolved in 100 mM bicine (pH of 7.3). The substrates were mildly agitated while immersed in the phloroglucinol solution at room temperature for about 24 hours. The substrates were removed from the solution and rinsed with FDW. The resulting phloroglucinol-treated substrates were immersed in a 50 mM solution of silver nitrate. The substrates were mildly agitated while immersed in the silver nitrate solution at room temperature for about 60 hours. The polymeric substrates darkened in color denoting the deposition of silver metal onto the polymeric substrates. The metallization of the silver is due to the reducing capacity of the phloroglucinol layer on the substrate.

Thus, Example 20 illustrates how the immobilization of phloroglucinol onto polyisoprene, polycarbonate and polysulfone substrates was achieved according to the invention.

Example 21

Immobilization of Chitosan onto an Oxidized Polydimethylsiloxane Substrate

An antibacterial active agent, chitosan, is immobilized onto a polydimethylsiloxane (PDMS) substrate. The surface of a substrate comprising polydimethylsiloxane is oxidized by treating the surface of the substrate with a solution of $H_2O_2$/HCl in a volume ratio of 1:1 for about 5 minutes, followed by rinsing with water and ethanol thereby introducing reactive moieties (hydroxyl groups) on the surface of the substrate. The oxidized substrate is immersed in a solution of 1.1 mg/ml gallic acid dissolved in 100 mM Bicine (pH of 7.3). The substrate is mildly agitated while immersed in the gallic acid solution at room temperature for about 24 hours. The substrate is removed from the solution and rinsed with filtered, distilled water. The resulting gallic acid-treated substrate is immersed in a solution of chitosan (1 mg/ml) dissolved in 300 mM acetate and 600 mM sodium chloride solution (pH 4.5). The gallic acid-treated substrate is mildly agitated while immersed in the chitosan solution at room temperature for 24 hours. The substrate is removed from the chitosan solution and washed with filtered, distilled water resulting in an oxidized PDMS substrate with chitosan immobilized on the surface thereof. Immobilization of Chitosan can be confirmed using, for example, a color assay or surface sensitive spectroscopy such as RAMAN, XPS contact angle, or ATR-FTIR.

Thus, Example 21 illustrates how the immobilization of chitosan onto a polydimethylsiloxane substrate can be achieved according to the invention.

Example 22

Immobilization of QUAT-chitosan onto an Oxidized Polydimethylsiloxane Substrate An antibacterial/antimicrobial active agent, QUAT-chitosan, is immobilized onto a polydimethylsiloxane (PDMS) substrate. Chitosan is initially modified with a quaternary ammonium cation (QUAT) resulting in a QUAT-chitosan. The surface of a substrate comprising polydimethylsiloxane is oxidized by treating the surface of the substrate with a solution of H₂O₂/HCl in a volume ratio of 1:1 for about 5 minutes, followed by rinsing with water and ethanol thereby introducing reactive moieties (hydroxyl groups) on the surface of the substrate. The oxidized substrate is immersed in a solution of 1.1 mg/ml gallic acid dissolved in 100 mM Bicine (pH of 7.3). The substrate is mildly agitated while immersed in the gallic acid solution at room temperature for about 24 hours. The substrate is removed from the solution and rinsed with filtered, distilled water. The resulting gallic acid-treated substrate is immersed in a solution of the QUAT-chitosan (1 mg/ml) dissolved in a 300 mM acetate and 600 mM sodium chloride solution (pH 4.5). The gallic acid-treated substrate is mildly agitated while immersed in the QUAT-chitosan solution at room temperature for about 24 hours. The substrate is removed from the QUAT-chitosan solution and rinsed with filtered, distilled water resulting in an oxidized PDMS substrate with a QUAT-chitosan conjugate immobilized on the surface thereof. Immobilization of Chitosan can be confirmed using, for example, a color assay or surface sensitive spectroscopy such as RAMAN, XPS contact angle, or ATR-FTIR.

Thus, Example 22 illustrates how the immobilization of QUAT-chitosan onto a polydimethylsiloxane substrate can be achieved according to the invention.

Example 23

Immobilization of Chitosan onto a UV Irradiated Polydimethylsiloxane Substrate

An antibacterial active agent, chitosan, is immobilized onto a polydimethylsiloxane (PDMS) substrate. The surface of a substrate comprising polydimethylsiloxane is contacted with a solution of benzophenone in acetone for about 5 minutes. The substrate is washed with water to remove the acetone. The substrate is then exposed to UV irradiation, so as to provide radicals on the surface of the substrate. The substrate is then immersed in a solution of 1.1 mg/ml gallic acid dissolved in 100 mM Bicine (pH of 7.3). The substrate is mildly agitated while immersed in the gallic acid solution at room temperature for about 24 hours. The substrate is removed from the solution and rinsed with filtered, distilled water. The resulting gallic acid-treated substrate is immersed in a solution of chitosan (1 mg/ml) dissolved in 300 mM acetate and 600 mM sodium chloride solution (pH 4.5). The gallic acid-treated substrate is mildly agitated while immersed in the chitosan solution at room temperature for about 24 hours. The substrate is removed from the chitosan solution and rinsed with filtered, distilled water resulting in an oxidized PDMS substrate with chitosan immobilized on the surface thereof. Immobilization of Chitosan can be confirmed using, for example, a color assay or surface sensitive spectroscopy such as RAMAN, XPS contact angle, or ATR-FTIR.

Thus, Example 23 illustrates how the immobilization of chitosan onto a polydimethylsiloxane substrate can be achieved according to the invention.

Example 24

Immobilization of a Chitosan-Gallic Acid Conjugate onto an Oxidized Polydimethylsiloxane Substrate An antibacterial active agent, chitosan, is immobilized onto a polydimethylsiloxane (PDMS) substrate. A chitosan-gallic acid conjugate solution is prepared by combining a solution of chitosan (1 mg/ml) dissolved in a 300 mM acetate and 600 mM sodium chloride solution (pH 4.5), with a solution of 1.1 mg/ml gallic acid in a 300 mM acetate and 600 mM (pH of 4.5). A substrate comprising polydimethylsiloxane is oxidized by treating the surface of the substrate with a solution of H₂O₂/HCl in a volume ratio of 1:1 for about 5 minutes, followed by rinsing with water and ethanol thereby introducing reactive moieties (hydroxyl groups) on the substrate. The oxidized substrate is immersed in the solution of chitosan-gallic acid conjugate. The substrate is mildly agitated while immersed in the chitosan-gallic acid conjugate solution at room temperature for about 24 hours. The substrate is removed from the solution and rinsed with filtered, distilled water resulting in an oxidized PDMS substrate with chitosan immobilized on the surface thereof. Immobilization of Chitosan can be confirmed using, for example, a color assay or surface sensitive spectroscopy such as RAMAN, XPS contact angle, or ATR-FTIR.

Thus, Example 24 illustrates how the immobilization of a chitosan-gallic acid conjugate onto a polydimethylsiloxane substrate can be achieved according to the invention.

Of course, other active agents, linker compounds, and compounds including trihydroxyphenyl groups could be used in the foregoing procedures.

What is claimed:

1. A substrate having an active agent immobilized on a surface thereof, the substrate having a compound including a trihydroxyphenyl group coupled to the substrate surface, wherein the compound includes an active agent coupled thereto, such that the active agent is immobilized on the surface, and the compound including a trihydroxyphenyl group is selected from the group consisting of gallic acid, phloroglucinol carboxylic acid, gallamide, benzenetriol, 5-methyl-benzene-1,2,3-triol, 3,4,5-trihydroxybenzaldehyde, 2,3,4-trihydroxybenzaldehyde, gallacetophenone, 3,4,5-trihydroxybenzamide, 2,3,4-trihydroxybenzoic acid, 5-hydroxydopamine hydrochloride, methyl gallate, pyrogallol, salts of the foregoing, and combinations thereof.

2. The substrate of claim 1, wherein the substrate is metal, inorganic oxide, ceramic, semiconductor or polymeric.

3. The substrate of claim 2, wherein the substrate comprises a non-metal substrate having a coating comprising metal.

4. The substrate of claim 2, wherein the substrate comprises a polymer selected from the group consisting of acrylonitrile butadiene styrenes, polyacrylonitriles, polyamides, polycarbonates, polyesters, polyetheretherketones, polyetherimides, polyethylenes, polyethylene terephthalates, polylactic acids, polymethyl methacrylates, polypropylenes, polystyrenes, polyurethanes, polyvinyl chloride, polyvinylidene chlorides, polyethers, polysulfones, silicones, polydimethylsiloxanes, polytetrafluoroethylene, and blends and copolymers thereof.

5. The substrate of claim 2, wherein the metal is selected from the group consisting of stainless steel, cobalt, titanium, nickel, zirconium, tantalum, chromium, tungsten, molybdenum, manganese, iron, vanadium, niobium, hafnium, aluminum, tin, palladium, ruthenium, iridium, rhodium, gold, silver, platinum, oxides of the foregoing, alloys of the foregoing, and combinations of the foregoing.

6. The substrate of claim 1, further comprising a linker compound coupled to the trihydroxyphenyl group, wherein the linker compound includes an active agent coupled thereto, thereby forming a substrate with an active agent immobilized on the surface thereof.

7. The substrate of claim 1, wherein the active agent is selected from the group consisting of antimicrobial agents, antifouling agents, anticoagulants, anti-inflammatory agents, and antithrombogenic agents.

8. The substrate of claim 1, wherein the active agent comprises an antimicrobial agent and the antimicrobial agent is an antibacterial agent.

9. The substrate of claim 1, wherein the active agent comprises an anti-inflammatory agent and the anti-inflammatory agent is a complement inhibitor.

10. The substrate of claim 1, wherein the active agent is selected from the group consisting of chitosan, linear polyethylene glycol, looped polyethylene glycol, polyethylene glycol derivatives, polyvinylpyrrolidone, polyvinylpyrrolidone derivatives, fractionated heparin, unfractionated heparin, heparin derivatives, quaternary ammonium polymers, albumin, polyethylenimine, 4-hydroxycoumarin derivatives, and combinations of the foregoing.

11. The substrate of claim 1, wherein the trihydroxyphenyl group is covalently bound to the active agent.

12. A medical device comprising the substrate of claim 1.

13. The medical device of claim 12, wherein the medical device comprises an extracorporeal blood circuit or component of an extracorporeal blood circuit.

14. The medical device of claim 12, wherein the medical device is selected from the group consisting of tubing, fluid bags, septa, stopcocks, clamps, filters, catheters, needles, and cannulae.

15. The medical device of claim 12, wherein the medical device comprises tubing, the tubing comprises polydimethylsiloxane, the compound including a trihydroxyphenyl group comprises gallic acid, and the active agent comprises chitosan or heparin.

16. The medical device of claim 12, wherein the medical device substrate comprises polydimethylsiloxane and the polydimethylsiloxane is modified to include terminal hydroxyl groups.

17. The medical device of claim 12, wherein the substrate comprises stainless steel, the compound including a trihydroxyphenyl group comprises gallic acid, and the active agent comprises chitosan.

* * * * *